US007960350B2

(12) United States Patent
Robledo

(10) Patent No.: US 7,960,350 B2
(45) Date of Patent: Jun. 14, 2011

(54) COMPOSITION AND METHOD FOR THE TREATMENT OF EYE DISEASE

(75) Inventor: Emilio Robledo, Tijuana (MX)

(73) Assignee: ADER Enterprises, Inc., San Diego, CA (US)

( * ) Notice: Subject to any disclaimer, the term of this patent is extended or adjusted under 35 U.S.C. 154(b) by 1645 days.

(21) Appl. No.: 10/971,922

(22) Filed: Oct. 21, 2004

(65) Prior Publication Data

US 2005/0113311 A1 May 26, 2005

Related U.S. Application Data

(60) Provisional application No. 60/514,403, filed on Oct. 24, 2003.

(51) Int. Cl.
*A61K 38/05* (2006.01)
*A61K 31/415* (2006.01)
*A01N 43/50* (2006.01)

(52) U.S. Cl. ..................... 514/21.91; 514/400
(58) Field of Classification Search ............... 514/21.91, 514/400
See application file for complete search history.

(56) References Cited

U.S. PATENT DOCUMENTS

| | | | |
|---|---|---|---|
| 4,426,330 A | 1/1984 | Sears | |
| 4,534,899 A | 8/1985 | Sears | |
| 4,837,028 A | 6/1989 | Allen | |
| 5,013,556 A | 5/1991 | Woodle et al. | |
| 5,213,804 A | 5/1993 | Martin et al. | |
| 5,225,212 A | 7/1993 | Martin et al. | |
| 5,356,633 A | 10/1994 | Woodle et al. | |
| 5,512,592 A | 4/1996 | Zaloga et al. | |
| 5,540,935 A | 7/1996 | Miyazaki et al. | |
| 5,543,152 A | 8/1996 | Webb et al. | |
| 5,556,948 A | 9/1996 | Tagawa et al. | |
| 5,705,188 A | 1/1998 | Junichi et al. | |
| 5,795,912 A * | 8/1998 | Tsubota | 514/458 |
| 5,811,446 A * | 9/1998 | Thomas | 514/399 |
| 6,159,485 A * | 12/2000 | Yu et al. | 424/401 |
| 6,281,192 B1 * | 8/2001 | Leahy et al. | 514/8 |
| 6,629,970 B2 * | 10/2003 | Bagrov et al. | 604/521 |

FOREIGN PATENT DOCUMENTS

| | | |
|---|---|---|
| EP | 445131 B1 | 4/1994 |
| EP | 496813 B1 | 12/1994 |
| EP | 666753 B9 | 11/2000 |
| WO | WO8804924 A1 | 7/1988 |
| WO | WO9004384 A1 | 5/1990 |
| WO | WO9105545 A1 | 5/1991 |
| WO | WO9420073 A1 | 9/1994 |
| WO | WO9510294 A1 | 4/1995 |
| WO | WO9610391 A1 | 4/1996 |
| WO | WO9713499 A1 | 4/1997 |

OTHER PUBLICATIONS

Morris Baslow, Function of the N-Acetyl-L-Histidine System in the Vertebrate Eye, 10 J. Mol. Neurosci. 193 (1998).*
Shulin Ding, Recent Developments in Ophthalmic Drug Delivery, 1 PSTT 328 (Nov. 1998).*
MayoClinic.com, Cataracts Symptoms, available at http://www.mayoclinic.com/health/cataracts/DS00050/DSECTION=symptoms.*
Guidance for Industry: Container Closure Systems for Packaging Human Drugs and Biologics, U.S. Department of Health and Human Services, Food and Drug Administration, May 1999.*
Leo Chylack, et al, Classification of Human Senile Cataractous Change by the American Cooperative Cataract Research Group (CCRG) Method, 25 Inv. Ophthalmol. Vis. Sci. 174, (1984).*
Mark Babizhayev, Antioxidant Activity of L-Carnosine, a Natural Histidine-Containing Dipeptide in Crystalline Lens, 1004 Biochim. Biophysica Acta 363 (1989).*
International Search Report from PCT/US04/35021 dated Oct. 11, 2005.
Written Opinion of the International Searching Authority from PCT/US04/35021 dated Oct. 11, 2005.
Babizhayev, 1989 *Biochemica et Biophysica Acta* 1004:363-371.*
Babizhayev, 1996 *Clinica Chimica Acta* 254:1-21.*
Biros, et al. 2000. *J. Am. Vet. Med. Assoc.* 216:1780-6.*
Statistics on Vision Impairment: A Resource Manual, $5^{th}$ edition, Apr. 2002.*
Mican, Phil, "An interview with Mark Babizhayev Ph.D. about the development of NAC eye-drops" obtained from: http://www.antiaging-systems.com/ARTICLE-490/babizhayev-can-c-development.htm, on Oct. 18, 2010.
"Eye Medications" obtained from: http://www.uic.edu/com/eye/LearningAboutVision/EyeFacts/MedicineForEyes.shtml, on Oct. 18, 2010, dated Jan. 1, 1992.

* cited by examiner

*Primary Examiner* — Jeffrey S. Lundgren
*Assistant Examiner* — Sean Basquill
(74) *Attorney, Agent, or Firm* — Knobbe Martens Olson & Bear LLP

(57) ABSTRACT

Embodiments of the invention disclosed herein relate to methods of preventing and/or ameliorating one or more symptoms associated with an eye disease such as dry eye syndrome, cataracts of the eye and nuclear sclerosis of the eye lens by administering to a subject a therapeutically effective amount of Nα-acetyl-L-histidine. Additionally, provided herein are pharmaceutical compositions comprising Nα-acetyl-L-histidine. Kits for preventing and/or ameliorating one or more symptoms associated with an eye disease by administering a pharmaceutical composition comprising Nα-acetyl-L-histidine are also disclosed.

53 Claims, 15 Drawing Sheets

Before Treatment

After Treatment
( 26 Days )

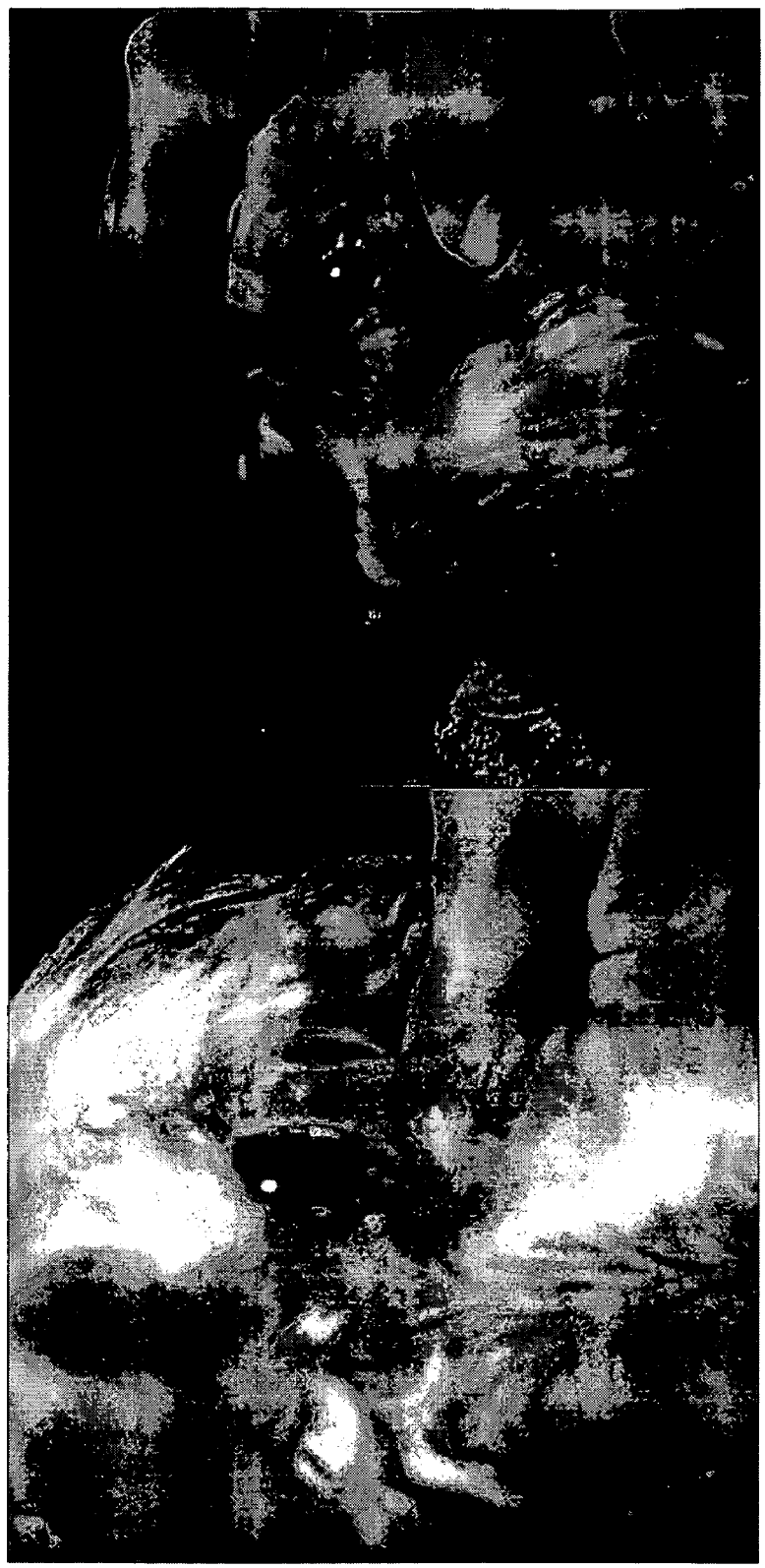
Figure 7A — Before Treatment
Figure 7B — After 15 days of treatment

COMPOSITION AND METHOD FOR THE TREATMENT OF EYE DISEASE

RELATED APPLICATIONS

This application is a nonprovisional application which claims priority under 35 U.S.C. §119(e) to U.S. Provisional Patent Application No. 60/514,403, entitled COMPOSITION AND METHOD FOR THE TREATMENT OF EYE DISEASE, filed Oct. 24, 2003, the disclosure of which is incorporated herein by reference in its entirety.

FIELD OF THE INVENTION

The field of the invention relates to the field of medicine and in particular to that of ophthalmology. More particularly, the invention relates to pharmaceutical compositions and methods that are useful in the treatment of eye diseases, such as cataracts, nuclear sclerosis of the eye lens and dry eye syndrome.

BACKGROUND

Throughout the world numerous people and animals suffer from a variety of eye diseases. Three prevalent eye diseases of both humans and animals are dry eye syndrome, eye cataracts and nuclear sclerosis of the eye lens. The initial effects of each of these eye diseases may be mild, however, if left untreated these diseases result in substantial morbidity and even complete vision loss.

One common eye disease among both humans and animals is dry eye syndrome. Dry eye syndrome is a general term used to describe a heterogeneous group of diseases resulting from inadequate wetting of the cornea and conjunctiva by the pre-corneal tear film (PCTF). Dry eye syndrome conditions are classified as various types of abnormalities that can lead to insufficient wetting of the corneal surface. The five major classifications are: (1) abnormalities of the aqueous layer, (2) abnormalities of the mucin layer, (3) abnormalities of the lipid layer, (4) abnormalities of the corneal epithelium and (5) abnormalities of the eye lids. Abnormalities in the aqueous layer caused by decreased tear production result in a condition known as keratoconjunctivitis sicca (KCS). Deficient mucin production results in uneven tear distribution whereas abnormalities of corneal epithelial morphology adversely affect tear film stability. Deficiencies in the lipid layer result in excessive tear evaporation and similarly, eye lid abnormalities result in excessive drying of the ocular surface.

The most common treatment for dry eye syndrome is the use of an artificial tear solution. Enhanced artificial tears containing zinc and bicarbonate have been developed to aid in the regeneration of mucin, tear film and epithelium. The main disadvantage to artificial tears is that they must be used several times per day.

Eye cataracts (cataracts) are defined as any opacity in the lens of the eye. The normal lens is translucent (clear) and it transmits and focuses light onto the retina in the back of the eye. A cataract within the lens may block the transmission of light to the retina. In both humans and animals, cataracts cause varying levels of vision impairment and may lead to blindness. Another eye disease that results in an opacity of the lens but which does not cause blindness is nuclear sclerosis of the eye lens. The incidence of nuclear sclerosis increases with age.

In the United States, a significant proportion of both people and animals are diagnosed with cataracts each year. For example, about 9.79 million dogs and 1.17 million cats have cataracts. In humans, cataracts are a leading cause of blindness. About 1 in 7 cases of blindness in adults over 45 can be attributed to cataracts (Statistics on Vision Impairment: A Resource Manual, $5^{th}$ edition, April 2002). Cataracts are also a leading cause of blindness worldwide. According to a World Health Organization Survey conducted in 1997, cataracts account for an estimated 16 million cases of blindness worldwide (Blindness and Visual Disability: Major Causes Worldwide, World Health Organization, 2001).

Currently, there is no medical treatment that is able to reverse cataracts. The most common treatment for cataracts is surgical removal. There are three principle surgical techniques that are used for cataract removal. The most common procedure is known as phacoemulsification. This technique has been widely performed on both humans and animals. In cases where a cataract is so hard that is cannot be efficiently phacoemulsified, a second technique known as extracapsular lens extraction is often used. In cases where a cataract is no longer held firmly in place in the eye, a technique known as intracapsular lens extraction is preferred.

Although cataract removal surgery has a high success rate, there are also several disadvantages. For example, when the eye is healthy, surgical procedures are usually effective, however, the success rate of surgery is greatly decreased if the eye is inflamed previous to or at the time of surgery. Moreover, complications associated with surgery, such as anterior uveitis and glaucoma are common. For example, in one study of 220 dogs (representing 346 eyes) that underwent cataract removal surgery, 134 of the 346 surgically treated eyes (38.8%) developed glaucoma within one year (Biros, et al. 2000. *J. Am. Vet. Med. Assoc.* 216:1780-6). In addition to such near-term complications, there are long-term complications of cataract removal surgery which are generally manifest as scarring of the lens capsule and detachment of the retina.

In addition to the above-mentioned surgical complications, cataract removal surgery is a relatively expensive eye surgery. For example, cataract removal surgery for one eye, including intraocular lens placement, typically costs about $2300.

In view of the above disadvantages associated with the current approaches for treating or reducing the symptoms associated with eye diseases, there exists a need for improvement.

SUMMARY

The present disclosure describes methods and compositions for ameliorating one or more symptoms associated with eye diseases which overcome at least one disadvantage of the prior art. Such eye diseases include, but are not limited to, dry eye syndrome (also referred to herein as dry eye), cataracts of the eye (also referred to herein as cataracts) and nuclear sclerosis of the eye lens (also referred to herein as nuclear sclerosis).

One embodiment of the invention provides a method of ameliorating at least one symptom associated with an eye disease by administering to a subject a therapeutically effective amount of Nα-acetyl-L-histidine. The administration of the Nα-acetyl-L-histidine ameliorates at least one symptom associated with an eye disease wherein the eye disease includes, but is not limited to, dry eye syndrome, cataracts of the eye and nuclear sclerosis of the eye lens. In some embodiments of the invention, β-alanyl-L-histidine (L-carnosine) is also administered to the subject. The administration of L-carnosine can be concurrent with or separate from the administration of Nα-acetyl-L-histidine. In some embodiments of the invention, Nα-acetyl-L-histidine or a combination or Nα-acetyl-L-histidine and L-carnosine are administered to the subject by injection, infusion, ingestion, inhalation, ophthalmically, orally or by topical application. Subjects that receive the Nα-acetyl-L-histidine or a combination of Nα-acetyl-L-histidine and L-carnosine can include, but are not limited to mammals, avians, amphibians, reptiles and other vertebrates. In some embodiments, the subjects are horses, pigs, dogs, cats, rodents and/or other companion pets. In other embodiments, the subjects are humans.

Another embodiment of the invention provides a method of ameliorating at least one symptom associated with an eye disease by administering to a subject a therapeutically effective amount of a composition comprising carboxymethylcellulose and Nα-acetyl-L-histidine. The administration of the composition ameliorates at least one symptom associated with an eye disease wherein the eye disease includes, but is not limited to, dry eye syndrome, cataracts of the eye and nuclear sclerosis of the eye lens. In some embodiments of the invention, β-alanyl-L-histidine (L-carnosine) is also administered to the subject.

Some embodiments of the invention also contemplate methods of preventing at least one symptom associated with an eye disease by administering to a subject a therapeutically effective amount of Nα-acetyl-L-histidine or a composition which comprises Nα-acetyl-L-histidine and carboxymethylcellulose. The administration of the Nα-acetyl-L-histidine or the composition which comprises Nα-acetyl-L-histidine and carboxymethylcellulose prevents at least one symptom associated with an eye disease wherein the eye disease includes, but is not limited to, dry eye syndrome, cataracts of the eye and nuclear sclerosis of the eye lens. In some embodiments of the invention, β-alanyl-L-histidine (L-carnosine) is also administered to the subject.

Some embodiments of the invention relate to a pharmaceutical composition comprising Nα-acetyl-L-histidine in a pharmaceutically acceptable carrier. In some embodiments, the pharmaceutical composition also comprises L-carnosine, carboxymethylcellulose or a combination of L-carnosine and carboxymethylcellulose. In certain embodiments of the invention, the pharmaceutically acceptable carrier is water, a buffer or a solution of sodium chloride. In some embodiments, the pharmaceutically acceptable carrier is sterile. In other embodiments, the pharmaceutically carrier is an ointment. In still other embodiments, the pharmaceutically acceptable carrier is a gel. Gels can be formulated using gel formulating materials that are well known in the art, including but not limited to, high viscosity carboxymethylcellulose, hydroxypropylmethylcellulose, polyethylene oxide and carbomer.

Certain embodiments of the invention also contemplate kits that comprise components useful for ameliorating and/or preventing a symptom associated with an eye disease. Such kits comprise a container comprising Nα-acetyl-L-histidine in a pharmaceutically acceptable carrier and instructions for administering the Nα-acetyl-L-histidine such that at least one symptom associated with the eye disease is ameliorated or prevented. Such eye diseases include, but are not limited to, dry eye syndrome, cataracts and nuclear sclerosis of the eye lens. In some embodiments, the kit also comprises L-carnosine and/or carboxymethylcellulose. In some embodiments, one or more of the kit components, such as Nα-acetyl-L-histidine, L-carnosine and/or carboxymethylcellulose, are formulated in a pharmaceutically acceptable carrier. In other embodiments, one or more of the kit components, such as Nα-acetyl-L-histidine, L-carnosine and/or carboxymethylcellulose, are provided separate from the pharmaceutically acceptable carrier then mixed prior to use. The containers included in some of the kits contemplated herein are droppers for the administration of eye drops. In other embodiments, the container is a tube for dispensing ointment or gel. In still other embodiments, the container is any appropriate container for drug delivery including, but not limited to, a syringe, a transdermal patch, a tablet, a capsule, an inhaler, a mister, an aerosolizer, or other container appropriate for delivery of a drug by injection, infusion, ingestion, inhalation, ophthalmically, orally or topical application.

Other aspects of the invention are contemplated in the numbered paragraphs that follow:

1. A method of ameliorating a symptom associated with an eye disease, said method comprising administering to a subject a therapeutically effective amount of Nα-acetyl-L-histidine, wherein the administration of said Nα-acetyl-L-histidine ameliorates at least one symptom associated with said eye disease.

2. The method of Paragraph 1, further comprising administering to said subject β-alanyl-L-histidine (L-carnosine).

3. The method of Paragraph 2, wherein said Nα-acetyl-L-histidine and β-alanyl-L-histidine (L-carnosine) are administered simultaneously to said subject.

4. The method of Paragraph 3, wherein both Nα-acetyl-L-histidine and β-alanyl-L-histidine (L-carnosine) are administered by providing to said subject a composition which comprises Nα-acetyl-L-histidine and β-alanyl-L-histidine (L-carnosine) each in a concentration from about 0.1% (w/v) to about 30% (w/v).

5. The method of Paragraph 3, wherein both Nα-acetyl-L-histidine and β-alanyl-L-histidine (L-carnosine) are administered by providing to said subject a composition which comprises Nα-acetyl-L-histidine in a concentration of about 1.2% (w/v) and β-alanyl-L-histidine (L-carnosine) in a concentration of about 1% (w/v).

6. The method of Paragraph 3, wherein both Nα-acetyl-L-histidine and β-alanyl-L-histidine (L-carnosine) are administered by providing to said subject a composition which comprises Nα-acetyl-L-histidine in a concentration of about 7.2% (w/v) and β-alanyl-L-histidine (L-carnosine) in a concentration of about 6% (w/v).

7. The method of Paragraph 1, wherein said eye disease is eye cataracts.

8. The method of Paragraph 1, wherein said eye disease is nuclear sclerosis of the eye lens.

9. The method of Paragraph 1, wherein said eye disease is dry eye syndrome.

10. The method of Paragraph 1, wherein said Nα-acetyl-L-histidine is administered to said subject by injection, infusion, ingestion, inhalation, ophthalmically, orally or by topical application.

11. The method of Paragraph 1, wherein said Nα-acetyl-L-histidine is administered to said subject ophthalmically.

12. The method of Paragraph 1, wherein said subject is selected from the group consisting of amphibians, reptiles, avians and mammals.

13. The method of Paragraph 12, wherein said mammal is selected from the group consisting of rodents, cats, dogs, pigs, horses and humans.

14. The method of Paragraph 12, wherein said mammal is a human.

15. The method of Paragraph 1, wherein said Nα-acetyl-L-histidine is administered at least one time per day.

16. The method of Paragraph 1, wherein said Nα-acetyl-L-histidine is administered more than one time per day.

17. The method of Paragraph 1, wherein said therapeutically effective amount of Nα-acetyl-L-histidine ranges from at least about 0.1 mg to at least about 3000 mg.

18. The method of Paragraph 1, wherein said therapeutically effective amount of Nα-acetyl-L-histidine ranges from at least about 1 mg to at least about 2000 mg.

19. The method of Paragraph 1, wherein said therapeutically effective amount of Nα-acetyl-L-histidine is at least about 1200 mg.

20. The method of Paragraph 1, wherein said therapeutically effective amount of Nα-acetyl-L-histidine is at least about 80 mg.

21. The method of Paragraph 1, wherein said Nα-acetyl-L-histidine is formulated in a solution.

22. The method of Paragraph 21, wherein said solution is ophthalmic solution.

23. The method of Paragraph 1, wherein said Nα-acetyl-L-histidine is formulated in an ointment.

24. The method of Paragraph 1, wherein said Nα-acetyl-L-histidine is formulated in a gel.

25. A method of ameliorating a symptom associated with an eye disease, said method comprising administering to a subject a therapeutically effective amount of a composition comprising carboxymethylcellulose and Nα-acetyl-L-histidine, wherein the administration of composition ameliorates at least one symptom associated with said eye disease.

26. The method of Paragraph 25, wherein said composition further comprises β-alanyl-L-histidine (L-carnosine).

27. The method of Paragraph 26, wherein said composition comprises Nα-acetyl-L-histidine and β-alanyl-L-histidine (L-carnosine) each in a concentration from about 0.1% (w/v) to about 30% (w/v).

28. The method of Paragraph 26, wherein said composition comprises Nα-acetyl-L-histidine in a concentration of about 1.2% (w/v) and β-alanyl-L-histidine (L-carnosine) in a concentration of about 1% (w/v).

29. The method of Paragraph 26, wherein said composition comprises carboxymethylcellulose in a concentration of about 0.5% (w/v), Nα-acetyl-L-histidine in a concentration of about 1.2% (w/v) and β-alanyl-L-histidine (L-carnosine) in a concentration of about 1% (w/v).

30. The method of Paragraph 26, wherein said composition comprises carboxymethylcellulose in a concentration of about 1% (w/v), Nα-acetyl-L-histidine in a concentration of about 7.2% (w/v) and β-alanyl-L-histidine (L-carnosine) in a concentration of about 6% (w/v).

31. The method of Paragraph 25, wherein said eye disease is eye cataracts.

32. The method of Paragraph 25, wherein said eye disease is nuclear sclerosis of the eye lens.

33. The method of Paragraph 25, wherein said eye disease is dry eye syndrome.

34. The method of Paragraph 25, wherein said composition is administered to said subject by injection, infusion, ingestion, inhalation, ophthalmically, orally or topical application.

35. The method of Paragraph 25, wherein said composition is administered to said subject ophthalmically.

36. The method of Paragraph 25, wherein said subject is selected from the group consisting of amphibians, reptiles, avians and mammals.

37. The method of Paragraph 36, wherein said mammal is selected from the group consisting of rodents, cats, dogs, pigs, horses and humans.

38. The method of Paragraph 36, wherein said mammal is a human.

39. The method of Paragraph 25, wherein said composition is administered at least one time per day.

40. The method of Paragraph 25, wherein said composition is administered more than one time per day.

41. The method of Paragraph 25, wherein said composition is formulated as a solution.

42. The method of Paragraph 41, wherein said solution is an ophthalmic solution.

43. The method of Paragraph 25, wherein said composition is formulated as an ointment.

44. The method of Paragraph 25, wherein said composition is formulated as a gel.

45. A pharmaceutical composition comprising Nα-acetyl-L-histidine in a pharmaceutically acceptable carrier.

46. The pharmaceutical composition of Paragraph 45, further comprising β-alanyl-L-histidine (L-carnosine).

47. The pharmaceutical composition of Paragraph 46, further comprising carboxymethylcellulose.

48. The pharmaceutical composition of Paragraph 47, wherein both Nα-acetyl-L-histidine and β-alanyl-L-histidine (L-carnosine) are present in a concentration from about 0.1% (w/v) to about 30% (w/v).

49. The pharmaceutical composition of Paragraph 47, wherein said Nα-acetyl-L-histidine is present in a concentration of about 1.2% (w/v), said β-alanyl-L-histidine (L-carnosine) is present in a concentration of about 1% (w/v) and said carboxymethylcellulose is present in a concentration of about 0.5% (w/v).

50. The pharmaceutical composition of Paragraph 47, wherein said Nα-acetyl-L-histidine is present in a concentration of about 7.2% (w/v), said β-alanyl-L-histidine (L-carnosine) is present in a concentration of about 6% (w/v) and said carboxymethylcellulose is present in a concentration of about 1% (w/v).

51. The pharmaceutical composition of Paragraph 45, wherein said pharmaceutically acceptable carrier is water.

52. The pharmaceutical composition of Paragraph 51, wherein said water is sterile.

53. The pharmaceutical composition of Paragraph 45, wherein said pharmaceutically acceptable carrier is a sodium chloride solution.

54. The pharmaceutical composition of Paragraph 53, wherein said sodium chloride solution is about 0.9% concentration.

55. The pharmaceutical composition of Paragraph 45, wherein said pharmaceutically acceptable carrier is an ointment.

56. The pharmaceutical composition of Paragraph 45, wherein said pharmaceutically acceptable carrier is a gel.

57. A kit for ameliorating a symptom associated with an eye disease, said kit comprising a container comprising Nα-acetyl-L-histidine in a pharmaceutically acceptable carrier and instructions for administering said Nα-acetyl-L-histidine such that said administration ameliorates at least one symptom associated with said eye disease.

58. The kit of Paragraph 57, wherein said Nα-acetyl-L-histidine is present in a concentration from about 0.1% (w/v) to about 30% (w/v).

59. The kit of Paragraph 57, wherein said Nα-acetyl-L-histidine is present in a concentration of about 1.2% (w/v).

60. The kit of Paragraph 57, wherein said eye disease is eye cataracts.

61. The kit of Paragraph 57, wherein said eye disease is nuclear sclerosis of the eye lens.

62. The kit of Paragraph 57, further comprising carboxymethylcellulose.

63. The kit of Paragraph 62, wherein said eye disease is dry eye syndrome.

64. The kit of Paragraph 57, wherein said container is a dropper.

65. The kit of Paragraph 57, wherein said container is a tube for dispensing ointment or gel.

66. A device for administering Nα-acetyl-L-histidine to the eye, said device comprising an interior portion comprising Nα-acetyl-L-histidine, the interior portion coupled to an applicator for transferring said Nα-acetyl-L-histidine from the interior portion to the eye.

67. The device of Paragraph 66, wherein said device is a dropper.

68. The device of Paragraph 66, wherein said device is a tube.

DETAILED DESCRIPTION

Figure 1A:
FIGS. 1A-D are photographs of dogs showing signs associated with dry eye syndrome.
Figure 1B:
Figure 1C:
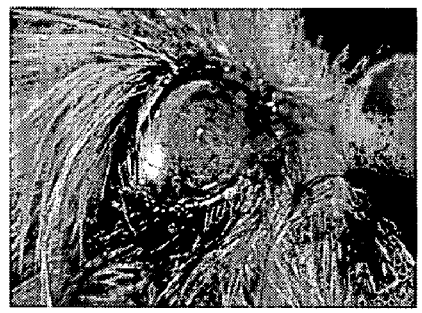
Figure 1D:
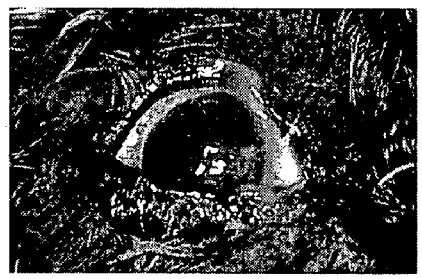
Figure 2A:
FIG. 2A is a photograph of a dog with a mature eye cataract (B) shows a dog with a hypermature cataract.
Figure 2B:
Figure 3A:
FIGS. 3A-D are photographs of dogs showing signs associated with nuclear sclerosis of the eye lens.
Figure 3B:
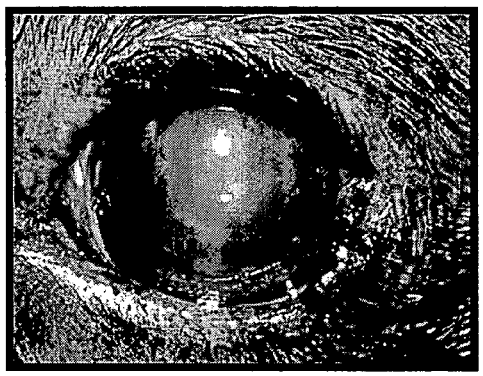
Figure 3C:
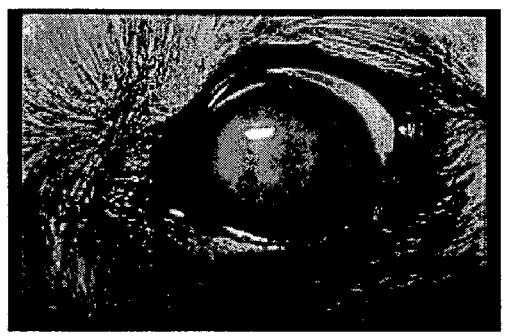
Figure 3D:

Embodiments of the invention described herein relate to methods and compositions for preventing and/or ameliorating one or more diseases of the eye. Some embodiments of the invention relate to methods of ameliorating at least one symptom associated with an eye disease such as dry eye syndrome (dry eye), cataracts of the eye (cataracts) or nuclear sclerosis of the eye lens (nuclear sclerosis). Additional embodiments of the invention relate to methods of preventing at least one symptom associated with an eye disease such as dry eye syndrome (FIGS. 1A-D), cataracts (FIGS. 2A-B) and nuclear sclerosis of the eye lens (FIGS. 3A-D). In each of the above embodiments, a composition comprising Nα-acetyl-L-histidine is administered to a subject in therapeutic amounts such that at least one symptom of the eye disease is either ameliorated or prevented.

Embodiments of the invention also relate to pharmaceutical compositions which comprise Nα-acetyl-L-histidine in a pharmaceutically acceptable carrier. In some embodiments of the invention, the pharmaceutical compositions can also comprise β-alanyl-L-histidine (L-carnosine) and/or carboxymethylcellulose.

Additional embodiments of the invention relates to kits useful in ameliorating and/or preventing at least one symptom associated with an eye disease such as dry eye syndrome, cataracts and nuclear sclerosis of the eye lens. Such kits comprise a container comprising Nα-acetyl-L-histidine in a pharmaceutically acceptable carrier.

Nα-acetyl-L-histidine

Nα-acetyl-L-histidine is a derivative of the naturally occurring amino acid L-histidine. Nα-acetyl-L-histidine can be synthesized from L-histidine and an acetyl donor using methods well known in the art. For example, Nα-acetyl-L-histidine can be prepared by the reaction of L-histidine with acetic anhydride under basic conditions. Additionally, various grades of Nα-acetyl-L-histidine can be easily obtained in bulk quantities from a variety of chemical manufacturers.

β-alanyl-L-histidine (L-carnosine)

L-carnosine is a dipeptide which consists of β-alanine linked to L-histidine via a peptide bond. L-carnosine is naturally occurring and it can be isolated from the muscle tissue of various species of vertebrates. Alternatively, L-carnosine can be synthesized by reacting β-alanine with a halogenated aromatic alcohol, such as pentafluorophenol, to give β-alanine pentafluorophenyl ester (see M. Bodansky in "The Practice of Peptide Synthesis", 1984). The resulting β-alanine derivative is then reacted with histidine methyl ester to produce a dipeptide ester. β-alanyl-L-histidine (L-carnosine) is finally obtained by hydrolysis of the ester. As an alternative to the above-described isolation and synthesis methods, various grades of L-carnosine can be obtained from commercial chemical suppliers in bulk quantities.

L-carnosine has been widely studied for its antioxidant properties. Given its status as an antioxidant, L-carnosine has been recommended by many as a nutritional supplement. In addition to its use as a nutritional supplement, L-carnosine has been studied to determine its efficacy as a treatment for eye cataracts (see Babizhayev, 1989 *Biochemica* et *Biophysica Acta* 1004:363-371). However, recent studies suggest that when administered directly to the eye, L-carnosine does not lead to accumulation in the aqueous humor of the eye or have any significant effect on eye cataracts beyond that of a placebo control (see Babizhayev, 1996 *Clinica Chimica Acta* 254:1-21).

Pharmaceutical Compositions

In some embodiments of the invention, pharmaceutical compositions of one or more therapeutic compounds, which include Nα-acetyl-L-histidine, L-carnosine, carboxymethylcellulose or combinations thereof, can be prepared by formulating one or more of these therapeutic compounds in a pharmaceutically acceptable carrier. As used herein, "pharmaceutically or therapeutically acceptable carrier" refers to a carrier medium which does not interfere with the effectiveness of the biological activity of the active ingredients and which is not toxic to the host or patient. The type of carrier which is used in the pharmaceutical preparation will depend on the method by which the therapeutic compounds are to be administered. Many methods of preparing pharmaceutical compositions for various routes of administration are well known in the art.

In some embodiments of the invention, pharmaceutical compositions are prepared by dissolving Nα-acetyl-L-histidine in an appropriate solvent. Appropriate solvents include, but are not limited to, water, saline solution (for example, 0.9% NaCl), buffered solutions, ointments, gels or other solvents. In certain embodiments, the solvents are sterile. Thus, a sterile pharmaceutical composition can be prepared by mixing sterile ingredients aseptically. Alternatively, a the sterile pharmaceutical composition can be prepared by first mixing the ingredients then sterilizing the final preparation.

In some embodiments of the invention, pharmaceutical compositions comprising a concentration of Nα-acetyl-L-histidine from about 0.1% (w/v) to about 30% (w/v) are contemplated. In additional embodiments, pharmaceutical compositions comprising a concentration of Nα-acetyl-L-histidine from about 0.2% (w/v) to about 20% (w/v) are contemplated. In other embodiments, pharmaceutical compositions comprise less than about 0.1% (w/v) of Nα-acetyl-L-histidine. The pharmaceutical compositions according to still other embodiments of the invention comprise about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 1.1% (w/v), about 1.2% (w/v), about 1.3% (w/v), about 1.4% (w/v), about 1.5% (w/v), about 1.6% (w/v), about 1.7% (w/v), about 1.8% (w/v), about 1.9% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), about 20% (w/v), about 21% (w/v), about 22% (w/v), about 23% (w/v), about 24% (w/v), about 25% (w/v), about 26% (w/v), about 27% (w/v), about 28% (w/v), about 29% (w/v), about 30% (w/v) or more than 30% (w/v) of Nα-acetyl-L-histidine.

Pharmaceutical compositions which comprise Nα-acetyl-L-histidine in combination with another therapeutic compound are also contemplated. For example, Nα-acetyl-L-histidine can be combine with L-carnosine and/or carboxymethylcellulose. The addition of L-carnosine to a pharmaceutical preparation of Nα-acetyl-L-histidine is especially useful for the treatment of cataracts and nuclear sclerosis of the eye lens. Although Nα-acetyl-L-histidine is alone efficacious for the treatment of eye diseases, such as dry eye syndrome, cataracts and nuclear sclerosis of the eye lens, the addition of L-carnosine produces an additive and potentially a synergistic effect in ameliorating one or more symptoms associated with eye diseases.

In some embodiments, pharmaceutical compositions contemplated herein comprise a concentration of L-carnosine from about 0.1% (w/v) to about 30% (w/v). In additional embodiments, pharmaceutical compositions contemplated herein comprise a concentration of L-carnosine from about 0.2% (w/v) to about 20% (w/v). In other embodiments, pharmaceutical compositions comprise less than about 0.1% (w/v) of L-carnosine. The pharmaceutical compositions according to still other embodiments of the invention comprise about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 1.1% (w/v), about 1.2% (w/v), about 1.3% (w/v), about 1.4% (w/v), about 1.5% (w/v), about 1.6% (w/v), about 1.7% (w/v), about 1.8% (w/v), about 1.9% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), about 20% (w/v), about 21% (w/v), about 22% (w/v), about 23% (w/v), about 24% (w/v), about 25% (w/v), about 26% (w/v), about 27% (w/v), about 28% (w/v), about 29% (w/v), about 30% (w/v) or more than 30% (w/v) of L-carnosine.

In some embodiments, carboxymethylcellulose can be added to a preparation of Nα-acetyl-L-histidine as a lubricant and also to increase the viscosity of the preparation. Carboxymethylcellulose is a polymer that is obtainable in a variety of viscosities depending on the average polymer molecular weight. The use of both low viscosity and high viscosity carboxymethylcellulose is compatible with the pharmaceutical preparations described herein. It will be appreciated that increasing the viscosity grade of carboxymethylcellulose and/or the amount of this polymer present in the preparation will increase the viscosity of the preparation. In some embodiments, the viscosity of the preparation is sufficient to form a gel.

Carboxymethylcellulose-containing solutions, gels and/or ointments can be easily administered and are well tolerated by the subject. A particularly useful combination for preventing and/or ameliorating one or more symptoms associated with eye diseases is a pharmaceutical composition which comprises Nα-acetyl-L-histidine, L-carnosine and the sodium salt of carboxymethylcellulose.

The concentration of carboxymethylcellulose in pharmaceutical compositions contemplated in certain embodiments of the invention is generally less than that of either Nα-acetyl-L-histidine or L-carnosine. It will be appreciated, however, that pharmaceutical compositions which comprise concentrations of carboxymethylcellulose greater than the concentration of Nα-acetyl-L-histidine or L-carnosine alone or in combination can be envisioned and are well within the scope of the invention. For example, pharmaceutical compositions comprising a concentration of carboxymethylcellulose from about 0.1% (w/v) to about 10% (w/v) can be prepared. According to some embodiments of the invention, pharmaceutical compositions comprise about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 2% (w/v), about 3% (w/v), about 4% (w/v), about 5% (w/v), about 6% (w/v), about 7% (w/v), about 8% (w/v), about 9% (w/v), about 10% (w/v) or more than 10% (w/v) of carboxymethylcellulose. For the preparation of liquid pharmaceutical compositions, the sodium salt of carboxymethylcellulose is useful. A particularly useful pharmaceutical composition comprises about 0.5% (w/v) solution of sodium carboxymethylcellulose. A particularly useful gel preparation comprises about 1% (w/v) high viscosity sodium carboxymethylcellulose. Although the sodium salt of carboxymethylcellulose is described, it will be understood that any pharmaceutically acceptable salt of carboxymethylcellulose can be utilized in the pharmaceutical compositions contemplated herein. By "pharmaceutically acceptable salts" is meant any of the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the therapeutic compounds described herein with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like. Where appropriate, other compounds described herein can be converted to their pharmaceutically acceptable salts prior to their use in the preparation of a pharmaceutical composition contemplated by the invention.

A skilled artisan will recognize that other materials that are known in the art as lubricating and/or gelling agents can be used in place of or in addition to carboxymethylcellulose. One example of gelling agents are carbomers, such as Carbopol 980NF® (Noveon). In some embodiments, Carbopol 980NF® and/or other carbomers are used alone or together with high viscosity carboxymethylcellulose to form ophthalmic gels. Typical concentrations of carbomer contained in such gel preparations range from about 0.1% (w/v) to about 10% (w/v). In some embodiments, carbomer is present in a concentration from about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 2% (w/v), about 3% (w/v), about 4% (w/v), about 5% (w/v), about 6% (w/v), about 7% (w/v), about 8% (w/v), about 9% (w/v), about 10% (w/v) or greater than about 10% (w/v). In a preferred embodiments, the gel is formulated with 0.3% Carbopol 980NF® and 1% high viscosity carboxymethylcellulose.

It will be appreciated that in some embodiments, the pharmaceutical compositions contemplated herein can comprise N$\alpha$-acetyl-L-histidine, L-carnosine and carboxymethylcellulose alone or in various combinations. For example, a particular useful pharmaceutical composition for preventing and/or ameliorating one or more symptoms associated with an eye disease comprises about 1.2% (w/v) N$\alpha$-acetyl-L-histidine, about 1% (w/v) L-carnosine and about 0.5% (w/v) carboxymethylcellulose. A particularly useful gel preparation comprises, for example, about 7.2% (w/v) N$\alpha$-acetyl-L-histidine, about 6% (w/v) L-carnosine and about 1% (w/v) high viscosity carboxymethylcellulose. It will also be appreciated that in some embodiments, the pharmaceutical compositions described herein can include additional ingredients which include, but are not limited to, preservatives and stabilizers. For example, some of the pharmaceutical compositions contemplated herein comprise about 0.01% (w/v) benzalkonium chloride as a preservative.

One of ordinary skill in the art will also appreciate that the pharmaceutical compositions contemplated in herein are not limited solutions gels and/or ointments. In some embodiments, the pharmaceutical compositions contemplated herein include various formulations that are known in the art. The following section provides a noncomprehensive description of such formulations and their methods of preparation.

The therapeutic compounds described herein can be formulated into any of many possible dosage forms such as, but not limited to, tablets, capsules, gel capsules, liquid syrups, soft gels, suppositories, and enemas. These compounds can also be formulated as suspensions in aqueous, non-aqueous or mixed media.

Pharmaceutical compositions that are particularly useful for administration directly to the eye include aqueous solutions and/or suspensions formulated as eye drops and thickened solutions and/or suspensions formulated as ophthalmic gels or ointments. Aqueous solutions and diluents for suspensions that are used in preparation of eye drops can include distilled water, physiological saline, and the like. Non-aqueous solutions and diluents for suspensions can include vegetable oil, liquid paraffin, mineral oil, propylene glycol, p-octyldodecanol as well as similar solvents.

Various additives may be contained in eye drops, ophthalmic gels and/or ophthalmic ointments as needed. These include, but not limited to, buffering agents, isotonizers, preservatives, thickeners, stabilizers, antizoxidants, pH-adjusting agents, chelating agents. Buffering agents are added to keep the pH constant and can include pharmaceutically acceptable buffering agents such as borate buffer, citrate buffer, tartrate buffer, phosphate buffer, and acetate buffer. Buffering agents are included in an amount that provides sufficient buffer capacity for the expected physiological conditions.

In addition to a buffer, isotonizers can be added to eye drops to make the preparation isotonic with the tear. Isotonizers include, but are not limited to, sugars such as glucose, sucrose and fructose; sugar alcohols such as mannitol and sorbitol; polyhydric alcohols such as glycerol, polyethylene glycol and propylene glycol; and salts such as sodium chloride, sodium citrate and sodium succinate. Isotonizers are added in an amount that makes the osmotic pressure of the eye drop equal to that of the tear.

Preservatives can be added to maintain the integrity of the eye drop and/or ophthalmic ointment. Examples of preservatives include, but are not limited to, benzalkonium chloride, parabens, chlorobutanol and benzylic alcohol.

In some embodiments, thickeners are used to increase the viscosity of ophthalmic preparations such as eye drops, ophthalmic gels and/or ophthalmic ointments. Thickeners that can be used include, but are not limited to, glycerol, polyethylene glycol and carboxyvinyl polymers.

In addition to the above, in some embodiments, it is desirable to use additional agents which include, but are not limited to, stabilizers such as sodium sulfite and propylene glycol; antioxidants such as ascorbic acid, sodium ascorbate, butylated hydroxy toluene (BHT), butylated hydroxyanisole (BHA), tocopherol, sodium thiosulfate; and/or chelating agents such as ethylene-diamine-tetra-acetic acid (EDTA), ethylene glycol-bis-(2-aminoethyl)-N,N,N',N'-tetraacetic acid (EGTA) and sodium citrate.

Eye drops, ophthalmic gels and/or ophthalmic ointments can be prepared by aseptic manipulation or alternatively sterilization is performed at a suitable stage of preparation. Sterilization methods can include, but are not limited to, heat sterilization, irradiation and filtration.

Ophthalmic ointments (eye ointments) can be aseptically prepared by mixing the active ingredient into a base that is used for preparation of eye ointments followed by formulation into pharmaceutical preparations with any method known in the art. Typical bases for eye ointments are exemplified by vaseline, jelene 50, plastibase and macrogol. In addition, surfactants may be added to increase hydrophilia.

Compositions and formulations for oral administration include powders or granules, microparticulates, nanoparticulates, suspensions or solutions in water or non-aquious media, capsules, gel capsules, sachets, tablets or minitablets. Thickeners, flavoring agents, diluents, emulsifiers, dispersing aids or binders may be desirable. In some embodiments, oral formulations are those in which the therapeutic compounds described herein are administered in conjunction with one or more penetration enhancers surfactants and chelators. In certain embodiments, surfactants include fatty acids and/or esters or salts thereof, bile acids and/or salts thereof. Exemplary bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Exemplary fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (for example, sodium). Some embodiments include combinations of penetration enhancers, for example, fatty acids/salts in combination with bile acids/salts. Another exemplary combination is the sodium salt of lauric acid, capric acid and UDCA. Further penetration enhancers include polyoxyethylene-9-lauryl ether, polyoxyethylene-20-cety-1 ether. The therapeutic compounds described herein can be delivered orally in granular form including sprayed dried particles, or complexed to form micro or nanoparticles. Complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Other exemplary complexing agents include chitosan, N-trimethylchitosan, poly-L-lysine, polyhistidine, polyomithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG).

Solid dosage forms for oral administration include capsules, tablets, pills, powders, and granules. In such solid dosage forms, the therapeutic compound is admixed with at least one inert pharmaceutically acceptable carrier such as sucrose, lactose, or starch. Such dosage forms can also comprise, as is normal practice, additional substances other than inert diluents, for example, lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations for parenteral intrathecal or intraventricular administration include sterile aqueous or non-aqueous solutions, suspensions, or emulsions. Examples of aqueous solvents include, but are not limited to, water, saline, Ringer's solution, dextrose solution, and 5% human serum albumin. Examples of non-aqueous solvents or vehicles include, but are not limited to, propylene glycol, polyethylene glycol, vegetable oils, such as olive oil and corn oil, gelatin, and injectable organic esters such as ethyl oleate. Additional examples of nonaqueous vehicles include liposomes. Parenteral dosage forms can contain adjuvants such as preserving, wetting, emulsifying, and dispersing agents and can contain additives that maintain isotonicity (for example, sodium chloride, mannitol) and chemical stability (for example, buffers and preservatives). They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

In one embodiment of the invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the invention.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The therapeutic compounds described herein can also be microencapsulated by, for example, the method of Tice and Bibi (in: Treatise on Controlled Drug Delivery, ed. A. Kydonieus, Marcel Dekker, N.Y. 1992, pp. 315-339), which is hereby incorporated by reference in its entirety.

The therapeutic compounds described herein can also be administered in a time release formulation, for example in a composition which includes a slow release polymer. These compounds can be prepared with carriers that will protect these compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be desirable. In some embodiments, topical formulations include those in which the therapeutic compounds described herein are in admixture with a topical delivery agent such as lipids, liposomes, fatty acids, fatty acid esters, steroids, chelating agents and surfactants. Exemplary lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). The therapeutic compounds described herein may be encapsulated within liposomes or may form complexes thereto, in particular to cationic liposomes. Alternatively, these compounds can be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (for example, isopropylmyristate, IPM), monoglyceride, diglyceride or pharmaceutically acceptable salt thereof.

Emulsions

In some embodiments of the invention, pharmaceutical compositions may be prepared and formulated as emulsions. Emulsions are typically heterogeneous systems of one liquid dispersed in another in the form of droplets usually exceeding 0.1 μm in diameter. (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the invention, a pharmaceutical composition comprising a therapeutic compound described herein is formulated as a microemulsion. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously. Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain ($C_8$-$C_{12}$) mono, di, and tri-glycerides, polyoxyethylated glyceryl fatty acid esters, fatty alcohols, polyglycolized glycerides, saturated polyglycolized $C_8$-$C_{10}$ glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions can form spontaneously when their components are brought together at ambient temperature. Microemulsions have also been effective in the transdermal delivery of active components in both cosmetic and pharmaceutical applications.

In some embodiments of the invention, microemulsions can also contain additional components and additives such as sorbitan monostearate (Grill 3), Labrasol, and penetration enhancers to improve the properties of the formulation and to enhance the absorption of the therapeutic compounds described herein. Penetration enhancers used in the microemulsions can be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used herein, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include, but are not limited to, the following: (1) liposomes obtained from natural phospholipids are biocompatible and biodegradable; (2) liposomes can incorporate a wide range of water and lipid soluble drugs; and (3) liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin and/or eye.

Several reports have detailed the ability of liposomes to deliver into the skin agents ranging from the size of small molecules to high-molecular weight DNA. Compounds including analgesics, antibodies, hormones and high-molecular weight DNAs have been administered to the skin. The majority of applications result in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap molecules rather than complex with them. pH-sensitive liposomes have been used to deliver various types of molecules to cells in experimental animals and cells in culture.

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, 2C.sub.1215G, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556, 948 (Tagawa et al.) describe PEG-containing liposomes that can be further derivatized with functional moieties on their surfaces.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Penetration Enhancers

In one embodiment, the invention employs various penetration enhancers to effect the efficient delivery of the therapeutic compounds described herein, to the skin or eye tissues of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.

Surfactants: In connection with the invention, surfactants (or "surface-active agents") are chemical entities which, when dissolved in an aqueous solution, reduce the surface tension of the solution or the interfacial tension between the aqueous solution and another liquid, with the result that absorption of therapeutic compounds through the mucosa is enhanced. In addition to bile salts and fatty acids, these penetration enhancers include, for example, sodium lauryl sulfate, polyoxyethylene-9-lauryl ether and polyoxyethylene-20-cetyl ether.

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (for example, oleate, laurate, caprate, myristate, palmitate, stearate, and linoleate).

Bile salts: The physiological role of bile includes the facilitation of dispersion and absorption of lipids and fat-soluble vitamins. Various natural bile salts, and their synthetic derivatives, act as penetration enhancers. Thus the term "bile salts" includes any of the naturally occurring components of bile as well as any of their synthetic derivatives. Exemplary bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE).

Chelating Agents: Chelating agents, as used in connection with the therapeutic compounds described herein, can be defined as compounds that remove metallic ions from solution by forming complexes therewith. For example, the chelation of metal ions can enhance the absorption of therapeutic compounds described herein through mucosa. Exemplary chelating agents include, but are not limited to, disodium ethylenediaminetetraacetate (EDTA), citric acid, salicylates (for example, sodium salicylate, 5-methoxysalicylate and homovanilate), N-acyl derivatives of collagen, laureth-9 and N-amino acyl derivatives of beta-diketones (enamines).

Non-chelating non-surfactants: As used herein, non-chelating non-surfactant penetration enhancing compounds can be defined as compounds that demonstrate insignificant activity as chelating agents or as surfactants but that nonetheless enhance absorption of the therapeutic compounds described herein through the alimentary mucosa. This class of penetration enhancers include, for example, unsaturated cyclic ureas, 1-alkyl- and 1-alkenylazacyclo-alkanone derivatives; and non-steroidal anti-inflammatory agents such as diclofenac sodium, indomethacin and phenylbutazone.

Agents that enhance uptake of therapeutic compounds at the cellular level may also be added to the pharmaceutical and other compositions of the invention. For example, cationic lipids, such as lipofectin (Junichi et al, U.S. Pat. No. 5,705,188), cationic glycerol derivatives, and polycationic molecules, such as polylysine can be used. Additionally, other agents may be utilized to enhance the penetration of the therapeutic compounds described herein, including glycols such as ethylene glycol and propylene glycol, pyrrols such as 2-pyrrol, azones, and terpenes such as limonene and menthone.

Other Components

The pharmaceutical compositions of the invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the invention, such as dyes, flavoring agents, preservatives, antioxidants, opacifiers, thickening agents and stabilizers. However, such materials, when added, should not unduly interfere with the biological activities of the therapeutic compounds of the invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the therapeutic compounds of the formulation.

Additionally, it will be appreciated that other pharmaceutical formulations, which can conveniently be presented in unit dosage form, can be prepared according to conventional techniques well known in the pharmaceutical industry. In general, such techniques include the step of bringing into association the active ingredients with the pharmaceutical carrier(s) or excipient(s). The formulations are typically prepared by uniformly and intimately bringing into association the active ingredients with liquid carriers or finely divided solid carriers or both, and then, if necessary, shaping the product.

Administration of Therapeutic Compound

The therapeutic compounds described herein, including the above-described pharmaceutical compositions, may be administered in a number of ways depending upon whether local or systemic treatment is desired and upon the area to be treated. Administration may be topical (including ophthalmic and to mucous membranes including vaginal and rectal delivery), pulmonary, (for example, by inhalation or insufflation of powders or aerosols, including by nebulizer) intratracheal, intranasal, epidermal, transdermal, oral or parenteral. Parenteral administration includes intravenous, intraarterial, subcutaneous, intraperitoneal or intramuscular injection or infusion; or intracranial, e.g., intrathecal or intraventricular, administration.

The compositions containing the therapeutic compounds described herein can be administered for preventative and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective amount". As used herein, "therapeutically effective amount" also means a dose that alleviates at least one of the signs, symptoms, or causes of a disease, or any other desired alteration of a biological system. In some embodiments of the invention, the result will, for example, involve preventing and/or ameliorating one or more symptoms associated with an eye disease. Amounts effective for this use will depend on the severity of the disease and the weight and general state of the patient.

In some embodiments of the invention, a therapeutic amount of Nα-acetyl-L-histidine or any of the other therapeutic compounds described herein ranges from at least about 0.1 mg to at least about 3000 mg. In other embodiments of the invention, a therapeutic amount of Nα-acetyl-L-histidine or any of the other therapeutic compounds described herein ranges from at least about 1 mg to at least about 2000 mg. In still other embodiments of the invention, a therapeutic amount of Nα-acetyl-L-histidine or any of the other therapeutic compounds described herein is at least about 2 mg, at least about 3 mg, at least about 4 mg, at least about 5 mg, at least about 6 mg, at least about 7 mg, at least about 8 mg, at least about 9 mg, at least about 10 mg, at least about 15 mg, at least about 20 mg, at least about 30 mg, at least about 40 mg, at least about 50 mg, at least about 60 mg, at least about 70 mg, at least about 80 mg, at least about 90 mg, at least about 100 mg, at least about 150 mg, at least about 200 mg, at least about 300 mg, at least about 400 mg, at least about 500 mg, at least about 600 mg, at least about 700 mg, at least about 800 mg, at least about 900 mg, at least about 1000 mg, at least about 1500 mg, at least about 2000 mg, at least about 2500 mg, at least about 3000 mg or more than 3000 mg.

In preventative applications, compositions containing the therapeutic compounds disclosed herein are administered to a patient susceptible to or otherwise at risk of a particular disease. Such an amount is defined to be a "prophylactically effective amount". In this use, the precise amounts again depend on the patient's state of health and weight, and can be readily determined by one of ordinary skill in the art. In some embodiments of the invention, the prophylactically effective amount is the same as the therapeutically effective amount.

In some embodiments of the invention, a subject having or who is at risk for an eye disease such as dry eye syndrome, cataracts or nuclear sclerosis of the eye lens is identified. Signs and symptoms of eye diseases such as dry eye syndrome, cataracts and nuclear sclerosis of the eye lens are apparent to those of skill in the art. Risk factors for such diseases include, but are not limited to, factors due to physical condition, heredity and pre-existing disease state (such as diabetes). Preferably the subject is human, however, animals that suffer from or who are at risk for an eye disease (animals in need of treatment) can also be identified by one skilled in the art. Mammals in need of treatment, such as cats, dogs, pigs, horses, cows and rodents can be identified. Additionally, animals such as avians, reptiles and amphibians that are in need of treatment can be identified.

In some embodiments of the invention, Nα-acetyl-L-histidine is administered to the identified subject in a therapeutically effective amount sufficient to ameliorate at least one symptom associated with an eye disease which includes, but is not limited to, dry eye syndrome, cataracts or nuclear sclerosis of the eye lens. In other embodiments of the invention, L-carnosine is also administered. The L-carnosine can be administered prior to, subsequent to or simultaneously with the administration of the Nα-acetyl-L-histidine. In still other embodiments of the invention, a composition comprising carboxymethylcellulose and Nα-acetyl-L-histidine can be administered to a subject in need thereof. L-carnosine can be administered prior to, subsequent to or simultaneously with the administration of the carboxymethylcellulose/Nα-acetyl-L-histidine composition.

In a preferred embodiment, a pharmaceutical composition comprising carboxymethylcellulose in a concentration of about 0.5% (w/v), Nα-acetyl-L-histidine in a concentration of about 1.2% (w/v), β-alanyl-L-histidine (L-carnosine) in a concentration of about 1% (w/v) and benzalkonium chloride in a concentration of about 0.01% (w/v) in a pharmaceutically acceptable carrier of about 0.9% sodium chloride is administered ophthalmically to a subject in the form of an eye drop. The eye drop is administered to the subject at the rate of two drops per eye two to three times each day in the affected eye(s). Typically, at least 8 ml total of the eye drop is administered to the subject over a one month period. However, it will be appreciated that more or less of the eye drop can be administered for periods shorter than or substantially longer than one month. During the course of administration and thereafter, at least one symptom of the eye disease is ameliorated.

In another preferred embodiment, a pharmaceutical gel composition comprising, high viscosity carboxymethylcellulose in a concentration of about 1% (w/v), Carbopol 980NF® in a concentration of about 0.3% (w/v), Nα-acetyl-L-histidine in a concentration of about 7.2% (w/v), β-alanyl-L-histidine (L-carnosine) in a concentration of about 6% (w/v) and benzalkonium chloride in a concentration of about 0.01% (w/v) in a pharmaceutically acceptable carrier of about 0.9% sodium chloride is administered ophthalmically to a subject at the rate of 1 drop per eye 3 times per day in the affected eye(s). Typically, 8 ml total of the gel is administered to the subject over a three month period. However, it will be appreciated that more or less of the gel preparation can be administered for periods shorter than or substantially longer than three months. During the course of administration and thereafter, at least one symptom of the eye disease is ameliorated.

Dosing

Formulation of the therapeutic compounds described herein and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of the particular pharmaceutical composition and the method of administration. Acceptable dosages can generally be estimated based on $EC_{50}$ (effective concentration for 50% of the test group) found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the therapeutic compositions described herein are administered in maintenance doses, ranging from 0.01 µg to 100 g per kg of body weight, once or more daily, to once every 20 years.

The pharmaceutical compositions described herein can be administered as a single dose or in multiple doses; administered either as individual therapeutic agents or in combination with other therapeutic agents; and combined with conventional therapies, which may be administered sequentially or simultaneously. In one embodiment of the invention, daily dosages in human and/or animal therapy of the present ophthalmic formulations are about 1 drop per eye, about 2 drops per eye, about 3 drops per eye, about 4 drops per eye, about 5 drops per eye, about 6 drops per eye, about 7 drops per eye, about 8 drops per eye, about 9 drops per eye, about 10 drops per eye, about 11 drops per eye, about 12 drops per eye or more than about 12 drops per eye. In another embodiment of the invention, daily administration schedule for the present ophthalmic formulations in human and/or animal therapy is about 1 time per day, about 2 times per day, about 3 times per day, about 4 times per day, about 5 times per day, about 6 times per day, about 7 times per day, about 8 times per day, about 9 times per day, about 10 times per day, about 11 times per day, about 12 times per day or more than about 12 times per day. Dosages can be standardized for instance by means of a standard pharmacopeial medicinal dropper of 3 mm in external diameter, which when held vertically delivers 20 drops of water of total weight of 0.9 to 1.1 grams at 25° C.

When administered according to the dosage schedule described above, the treatment regimen in humans and/or animals can continue indefinitely or until no further improvement is observed. Alternately, the treatment regimen can last for 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 60 days, 70 days, 80 days, 90 days, 100 days, 150 days, 200 days, 250 days, 300 days, 400 days, 500 days, 750 days, 1000 days or more than 1000 days.

Kits

Some embodiments of the invention relate to kits for preventing and/or ameliorating one or more symptoms associated with an eye disease. The kits can comprise one or more containers which contain one or more of the therapeutic compounds described herein. The compounds can be present in the container as a prepared pharmaceutical composition, or alternatively, the compounds can be unformulated. In such embodiments, the kit can include the unformulated compounds in a container that is separate from the pharmaceutically acceptable carrier. Prior to use, the compound in diluted or otherwise mixed with the pharmaceutically acceptable carrier.

Some embodiments of the kits provided herein also comprise instructions which describe the method for administering the pharmaceutical composition in such a way that one or more symptoms associated with an eye disease which includes, but is not limited to, dry eye syndrome, cataracts and/or nuclear sclerosis of the eye lens. In some embodiments, the instructions also describe the procedure for mixing the therapeutic compounds contained in the kit with a pharmaceutically acceptable carriers.

In some embodiments of the invention, the container which comprises the therapeutic compounds described herein is a container which is used for ophthalmic administration. In certain embodiments, the container is a dropper for administering eye drops. In other embodiments, the container is a tube for administering an ophthalmic gel or an ophthalmic ointment.

Some embodiments of this invention are further illustrated by the following examples which should not be construed as limiting. It will be appreciated by those of skill in the art that the techniques disclosed in the examples which follow represent techniques discovered by the inventor to function well in the practice of the embodiments of the invention described herein, and thus can be considered to constitute preferred modes for the practice of these embodiments. Those of skill in the art will, however, in light of the present disclosure, appreciate that many changes can be made in the specific embodiments which are disclosed herein and still obtain a like or similar result without departing from the spirit and scope of the invention.

Devices

Some embodiments of the invention relate to devices for administering Nα-acetyl-L-histidine to a subject. In some embodiments, the devices include and interior portion, cavity or reservoir that contains Nα-acetyl-L-histidine formulated in a pharmaceutically acceptable carrier. In such embodiments, the pharmaceutically carriers include, but are not limited to, solutions, gels and ointments. In certain embodiments, the interior portion, cavity or reservoir contains one or more of the Nα-acetyl-L-histidine-containing pharmaceutical preparations described herein.

In some embodiments, the devices contemplated herein also comprise an applicator which is coupled to the interior portion, cavity or reservoir of the device. The applicator can be cylindrical, conical or any other shape which permits the Nα-acetyl-L-histidine-containing pharmaceutical preparation to be delivered from the interior portion, cavity or reservoir to the eye. In a preferred embodiment, the applicator is a tapered cylinder wherein the wide end is coupled to the interior portion, cavity or reservoir and the tapered end forms the exit opening for passage of the Nα-acetyl-L-histidine-containing pharmaceutical preparation to the eye.

Example 1

Preparation of a Pharmaceutical Composition Comprising Nα-acetyl-L-histidine

A pharmaceutical eye drop for the administration of therapeutic compounds described herein was prepared. Nutraceutical grade Nα-acetyl-L-histidine, β-alanyl-L-histidine (L-carnosine) were obtained as white crystalline powders (ARCOS, Mexico). United States Pharmacopoeia (USP) grade carboxymethylcellulose and benzalkonium chloride were obtained as a white powder (ARCOS, Mexico).

To prepare the carrier solution, one liter of a 0.9% (w/v) saline solution was prepared by adding 9 g of NaCl to a sufficient volume of deionized water to make 1 L of solution. After thorough mixing, the saline solution was sterilized.

One hundred milliliters (100 ml) of the pharmaceutical eye drop was prepared by aseptically adding 0.5 g of sodium carboxymethylcellulose, 1 g of Nα-acetyl-L-histidine, 0.85 g of L-carnosine and 0.01 g of benzalkonium to a sufficient volume of sterile saline solution to bring the final volume to 100 ml. The solution was mixed until all solids were completely dissolved then dispensed into sterile dropper bottles in 8 ml aliquots.

The next Example describes the preparation of an ophthalmic gel comprising Nα-acetyl-L-histidine.

Example 2

Preparation of a Pharmaceutical Composition Comprising Nα-acetyl-L-histidine

A pharmaceutical eye drop for the administration of therapeutic compounds described herein was prepared. Nutraceutical grade Nα-acetyl-L-histidine, β-alanyl-L-histidine (L-carnosine) were obtained as white crystalline powders (ARCOS, Mexico). United States Pharmacopoeia (USP) grade high viscosity carboxymethylcellulose and benzalkonium chloride were obtained as a white powder (ARCOS, Mexico).

To prepare the carrier solution, one liter of a 0.9% (w/v) saline solution was prepared by adding 9 g of NaCl to a sufficient volume of deionized water to make 1 L of solution. After thorough mixing, the saline solution was sterilized.

One hundred milliliters (100 ml) of the pharmaceutical eye gel was prepared by aseptically adding 1 g of high viscosity sodium carboxymethylcellulose, 7.2 g of Nα-acetyl-L-histidine, 6 g of L-carnosine, 0.3 g of Carbopol 980NF® and 0.01 g of benzalkonium to a sufficient volume of sterile saline solution to bring the final volume to 100 ml. The resulting gel was mixed until all solids were completely dissolved then dispensed into sterile dispensers in 8 ml aliquots.

The next Example describes ophthalmic administration of the eye drop of Example 1 to a dog suffering from eye cataracts.

Example 3

Figure 4B:
FIG. 4A is a photograph of a dog having an eye cataract; (B) close up of the eye cataract; (C) close up of the same eye after one week of treatment with a pharmaceutical composition comprising Nα-acetyl-L-histidine.

Short Term Ophthalmic Administration of a Pharmaceutical Composition Comprising Nα-acetyl-L-histidine for the Treatment of Cataracts in Dogs A dog having a cataract in the left eye was treated with the eye drop formulation prepared in Example 1. FIG. 4B shows the left eye of the dog prior to beginning a seven day treatment regimen. The cataract can be clearly seen as the compact white area in the center of the eye.

Figure 4C:
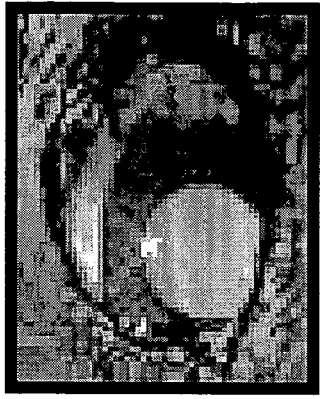
Figure 4A:

The dog in FIG. 4A was administered the eye drop formulation of Example 1 for seven days. The dosage was two drops twice each day for the seven day treatment course. The eye drops were administered directly to the center of the left eye whereas the right eye was left untreated. FIG. 4C is a close up photograph of the dog's left eye seven days after treatment with the eye drop. From this photograph, it can be clearly seen that the cloudy appearance around the periphery of the eye has cleared and compact white mass in the center of the eye has become much more diffuse indicating the initial stages of the disintegration ("melting away") of the cataract.

The next Example describes treatment of a dog for 26 days with the eye drop prepared in Example 1.

Example 4

Figure 5A:
FIG. 5A is a close up photograph of a dog's eye with a cataract prior to treatment; (B) a close up of the same eye after 26 days of treatment with a pharmaceutical composition comprising Nα-acetyl-L-histidine.

Ophthalmic Administration of a Pharmaceutical Composition Comprising Nα-acetyl-L-histidine for the Treatment of Cataracts/Nuclear Sclerosis in Dogs A dog having a cataract/nuclear sclerosis in the left eye was treated with the eye drop formulation prepared in Example 1. FIG. 5A shows the left eye of the dog prior to beginning a 26 day treatment regimen. The cataract/nuclear sclerosis can be clearly seen as the large concentrated white area in the center of the eye.

Figure 5B:

The dog depicted in FIGS. 5A-B was administered the eye drop formulation of Example 1 for 26 days. The dosage was two drops twice each day for the 26 day treatment course. The eye drops were administered directly to the center of the left eye whereas the right eye was left untreated. FIG. 5B is a close up photograph of the dog's left eye 26 days after treatment with the eye drop. From this photograph, it can be clearly seen that the cataract/nuclear sclerosis was substantially disintegrated (melted). The cortical appearance of cataract reversal starts from the periphery, and the lens of the eye has become much more transparent. After 26 days of treatment the size of the cataract or nuclear sclerosis has been substantially reduced. In addition to the actual physical reduction in the size of the cataract or nuclear sclerosis, the visual behavior of the dog was substantially improved.

The next Example describes treatment of a dog for a duration sufficient to completely eliminate a cataract.

Example 5

Figure 6A:
FIG. 6A is a photograph showing a dog's eye with a cataract prior to treatment; (B) the same eye during the course of treatment with a pharmaceutical composition comprising Nα-acetyl-L-histidine; (C) the same eye after completion of the course of treatment with a pharmaceutical composition comprising Nα-acetyl-L-histidine.

Ophthalmic Administration of a Pharmaceutical Composition Comprising Nα-acetyl-L-histidine for the Substantial Elimination of Cataracts in Dogs A dog having a cataract in the right eye was treated with the eye drop formulation prepared in Example 1. FIG. 6A shows the right eye of the dog prior to beginning a 36 day treatment regimen. The cataract can be clearly seen as the dense white area in the center of the eye.

Figure 6B:
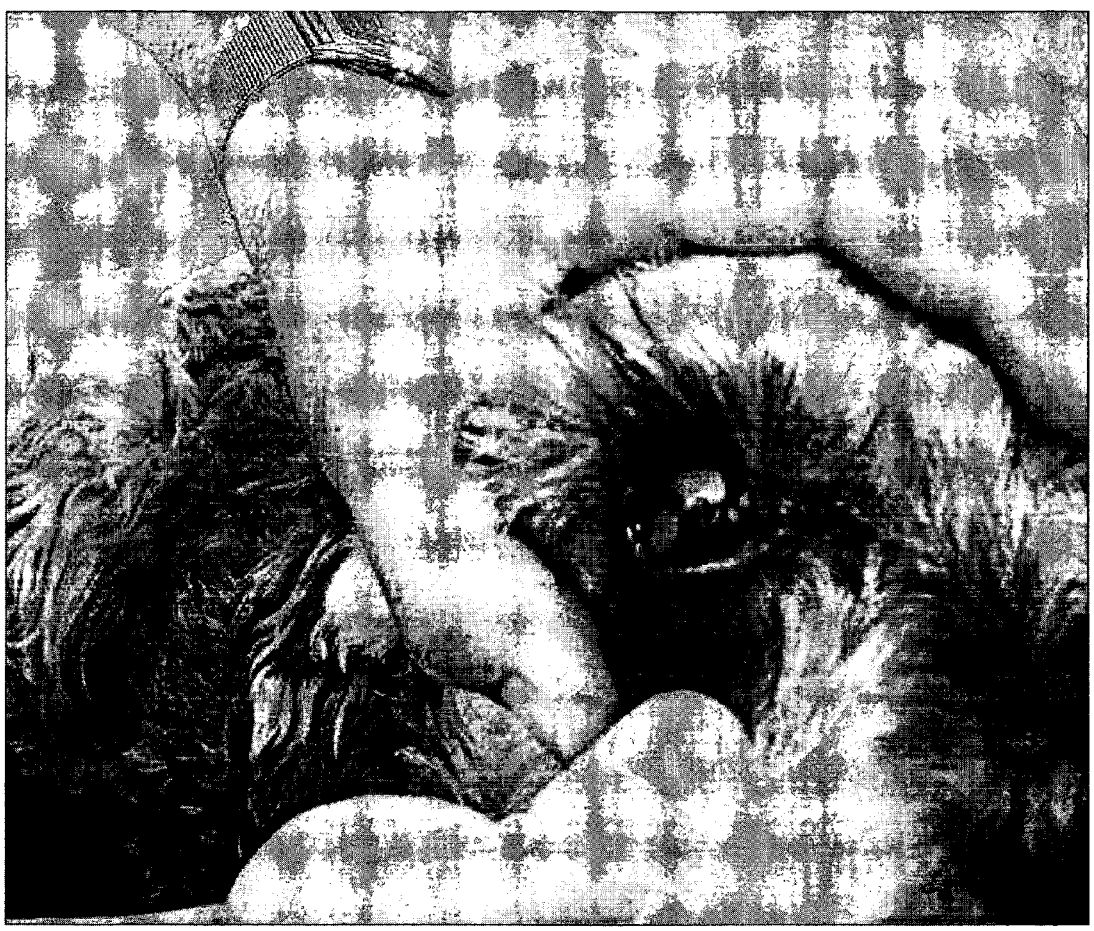
Figure 6C:

The dog depicted in FIGS. 6A-C was administered the eye drop formulation of Example 1 for 36 days. The dosage was two drops twice each day for the 36 day treatment course. The eye drops were administered directly to the center of the right eye whereas the left eye remained untreated. FIG. 6B is a close up photograph of the dog's right eye 14 days after treatment with the eye drop. From this photograph, it can be clearly seen that the cataract was substantially disintegrated (melted) and had a multilobal appearance spread diffusely within eye. After 36 days of treatment, the cataract appeared to be completely eliminated upon visual inspection and the entire eye was shiny and transparent (FIG. 6C). In addition to the elimination of the cataract, the visual behavior of the dog was substantially improved.

The next Example describes the administration of an eye drop comprising 1.2% (w/v) Nα-acetyl-L-histidine.

Example 6

Ophthalmic Administration of a Pharmaceutical Composition Comprising an Increased Concentration of Nα-acetyl-L-histidine A dog having a senile cataract in the left eye was treated with an eye drop formulation similar to that prepared in Example 1 except Nα-acetyl-L-histidine was present at a final concentration of 1.2% (w/v) and L-carnosine was present at a final concentration of 1% (w/v). FIG. 7A shows the left eye of the dog prior to beginning a 15 day treatment regimen. The senile cataract can be seen as a concentrated white area throughout the eye.

The dog depicted in FIGS. 7A-B was administered the above-described eye drop formulation for 15 days. The dosage was two drops thrice each day for the 15 day treatment course. The eye drops were administered directly to the center of the left eye whereas the right eye was left untreated. FIG. 7B is a close up photograph of the dog's left eye 15 days after treatment with the eye drop. From this photograph, it can be seen that the senile cataract was substantially disintegrated, particularly around its periphery. Furthermore, shortly after beginning the treatment, an increase in the lens transparency of the left eye was observed. After 15 days of treatment, the percent opacity eye lens was significantly reduced.

Figure 7D:
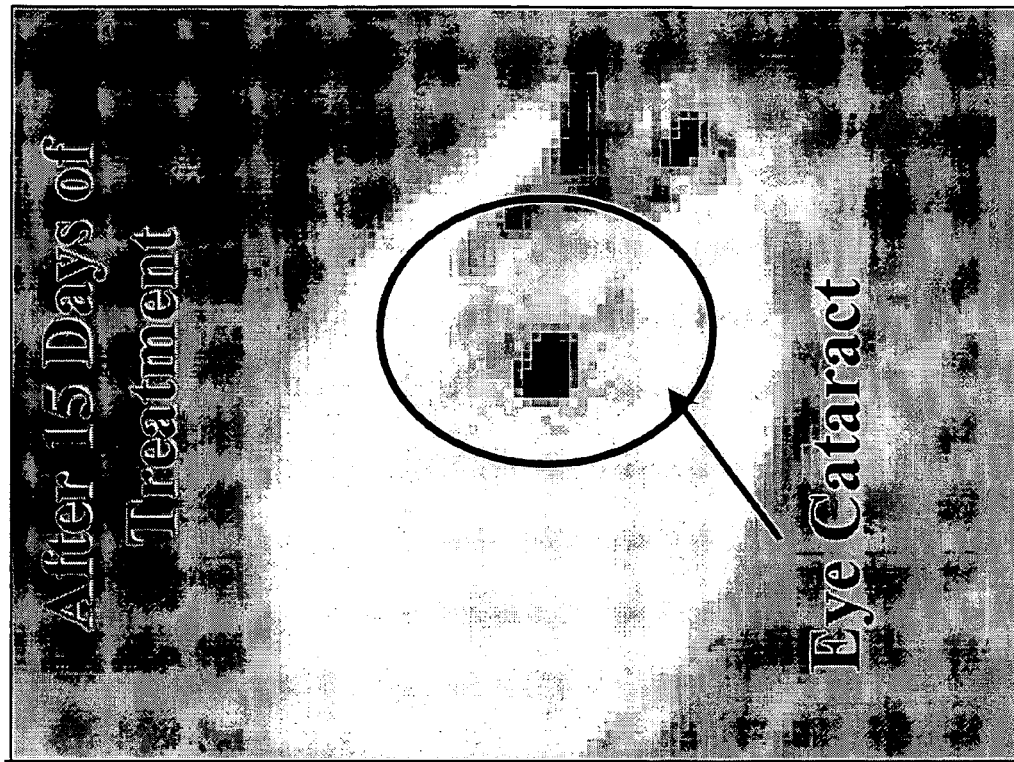
FIG. 7A is a photograph showing a dog's eye with a senile cataract prior to treatment; (B) the same eye after 15 days of treatment with a pharmaceutical composition comprising Nα-acetyl-L-histidine; (C) negative image showing the extent of the senile cataract in (A); (D) negative image showing the extent of the senile cataract in (B).
Figure 7C:
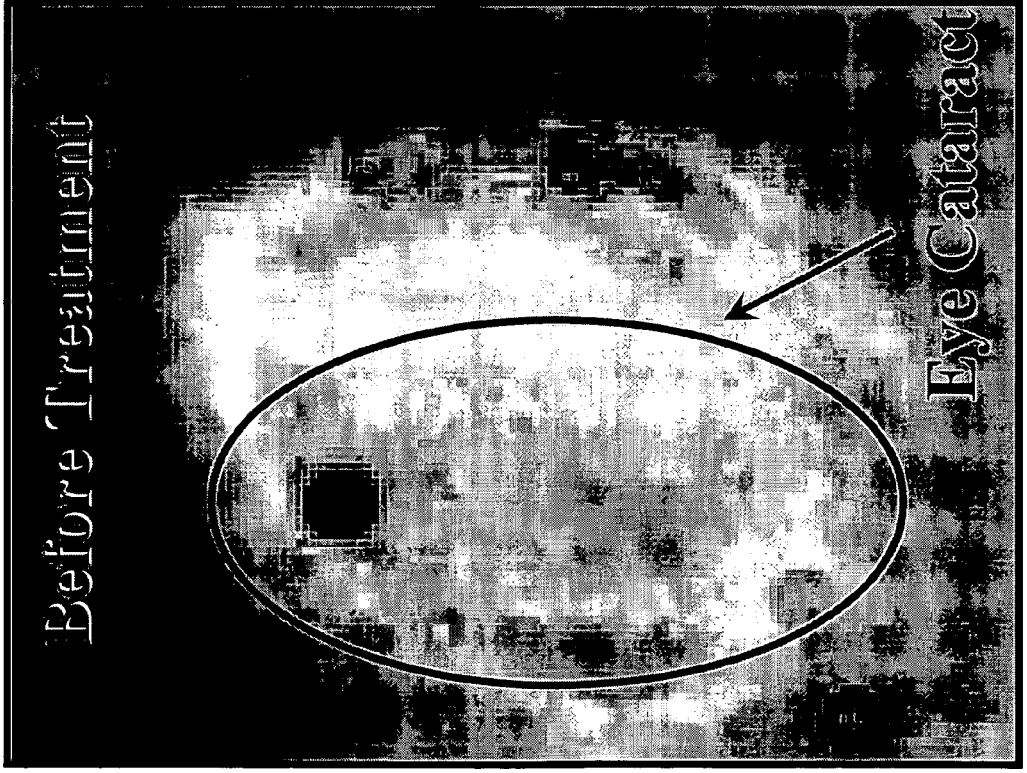

Negative images of each of the above photographs (FIGS. 7A-B) are shown in FIGS. 7C-D. In each case, an oval is traced around the periphery of the cataract. A comparison of FIG. 7C with FIG. 7D shows that the cataract has substantially decreased in size by the end of the 15 day treatment.

The next Example describes treatment of a dog for a duration sufficient to eliminate signs associated with dry eye.

Example 7

Ophthalmic Administration of a Pharmaceutical Composition Comprising Nα-acetyl-L-histidine for the Treatment of Dry Eye in Dogs A dog displaying one or more signs associated with dry eye in one or both eyes is treated with the eye drop formulation prepared in Example 1. The treatment regimen is continued until the signs associated with dry eye are eliminated and the dog no longer displays signs of eye discomfort. FIGS. 1A-D show examples of signs associated with dry eye.

The dog displaying one or more signs associated with dry eye is administered the eye drop formulation of Example 1 for 36 days. The dosage is two drops twice each day for the 36 day treatment course. The eye drops are administered directly to the affected areas of the eye. By about 2-7 days into the treatment course, signs associated with dry eye are substantially reduced. By the end the treatment period, the signs associated with dry eye are eliminated and the dog shows no signs of significant eye discomfort.

The next Example describes treatment of pigs for a duration sufficient to eliminate signs associated with cataracts, nuclear sclerosis or dry eye.

Example 8

Ophthalmic Administration of a Pharmaceutical Composition Comprising Nα-acetyl-L-histidine for the Treatment of Cataracts Nuclear Sclerosis or Dry Eye in Pigs Pig eye is generally accepted as a reliable model of the structure and function of the human eye. Results of experiments performed in the pig eye model system can be successfully extrapolated to determine the results in a human eye system. As such, experiments are conducted using the pig eye system to determine the success of the pharmaceutical composition of Example 1 in the treatment of one or more symptoms associated with cataracts, nuclear sclerosis or dry eye.

A first group of pigs, which display one or more signs associated with cataracts, nuclear sclerosis or dry eye in one or both eyes (treatment group), is treated with the eye drop formulation prepared in Example 1. The treatment regimen is continued until the signs associated with cataracts, nuclear sclerosis or dry eye are substantially diminished or eliminated or until the pigs no longer displays signs of eye discomfort or vision impairment. A second group of pigs, which does not show any signs associated with cataracts, nuclear sclerosis or dry eye in either eye (control group 1), is also treated with the eye drop formulation prepared in Example 1. Additionally, a third group of pigs, which shows one or more signs associated with cataracts, nuclear sclerosis or dry eye in one or both eyes (control group 2), is not treated with the eye drop formulation prepared in Example 1, but rather is administered a saline placebo. Diseased animals from the treatment group and control group 2 are carefully selected so that the outward manifestation of eye disease is as similar as possible between the two groups. Animals in control group 1, are selected such that they have similar physical characteristics to the animals in the treatment group and in control group 2.

The pigs of the treatment group and control group 1 are administered the eye drop formulation of Example 1 for 36 days. The dosage is two drops twice each day for the 36 day treatment course. The eye drops are administered directly to the affected area of the eye. By the end the treatment period, one or more signs associated with cataracts, nuclear sclerosis or dry eye are substantially reduced or eliminated in the animals of the treatment group whereas the signs associated with cataracts, nuclear sclerosis or dry eye either significantly worsen or do not change for the animals of control group 2 (placebo treated animals). The animals of control group 1 suffer no adverse reaction from the 36 day treatment regimen.

The next Example describes treatment of a horse using the gel formulation described in Example 2.

Example 9

Figure 8A:
FIG. 8A is a photograph showing a horse's eye with a traumatic cataract prior to treatment; (B) the same eye after 24 days of treatment with a pharmaceutical gel composition comprising Nα-acetyl-L-histidine; (C) the same eye after 44 days of treatment with a pharmaceutical composition comprising Nα-acetyl-L-histidine; (D) the same eye after 92 days of treatment with a pharmaceutical composition comprising Nα-acetyl-L-histidine.
Figure 8B:

Ophthalmic Administration of an Ophthalmic Gel Comprising Nα-acetyl-L-histidine for the Treatment of Cataracts in Horses A horse having a traumatic cataract in the right eye was treated with the eye drop formulation prepared in Example 2. FIG. 8A shows the right eye of the horse prior to beginning a 92 day treatment regimen. The traumatic cataract can be seen as the dense white area in the center of the eye.

Figure 8C:
Figure 8D:

The horse depicted in FIGS. 8A-D was administered the ophthalmic gel of Example 2 for 92 days. The dosage was 2 drops of gel, 3 times per day for the 92 day treatment course. The eye drops were administered directly to the center of the right eye whereas the left eye remained untreated. A close up photograph of the horse's right eye 24 days after treatment with the ophthalmic gel (FIG. 8B) shows that there was some noticeable reduction in the size and density of the traumatic cataract. After 44 days, much of the cataract has disappeared (FIG. 8C). At the end of the 92 day treatment, the cataract appeared to be almost completely eliminated upon visual inspection and the entire eye was shiny and transparent (FIG. 8D). In addition to the elimination of the cataract, the visual behavior of the horse was substantially improved.

The next Example describes treatment of a human volunteer for a duration sufficient to ameliorate one or more symptoms associated with cataracts.

Example 10

Ophthalmic Administration of a Pharmaceutical Composition Comprising Nα-acetyl-L-histidine for the Treatment of Cataracts in Humans A female human volunteer of age 65 having cataracts in each eye and suffering from substantial vision impairment was treated with the eye drop formulation prepared in Example 1. In particular, the volunteer was administered the eye drop formulation of Example 1 for 96 days. The dosage was two drops twice each day for the 96 day treatment course. The eye drops were administered directly to the center of each eye. After 96 days of treatment the volunteer's cataracts were substantially eliminated from each of his eyes. Furthermore, each eye was shiny and transparent. In addition to the actual physical disintegration of the cataract, the vision of the volunteer was substantially improved. For example, prior to the treatment with the eye drops, the volunteer could not see well enough to drive an automobile at night. After completion of the treatment regimen, the volunteer could see well enough to drive at night without significant difficulty.

The next Example describes treatment of a human volunteer for a duration sufficient to eliminate one or more symptoms associated with traumatic cataracts.

Example 11

Ophthalmic Administration of a Pharmaceutical Composition Comprising Nα-acetyl-L-histidine for the Treatment of Traumatic Cataracts in Humans This Example describes the treatment of a traumatic cataract in the human eye. The treatment extended for a duration sufficient to ameliorate at least some of the signs and symptoms associated with traumatic cataracts.

A diabetic male volunteer of age 74 having a traumatic cataract in the right eye (for at least 20 years) and suffering from substantial vision impairment was treated with the eye drop formulation prepared in Example 1. In particular, the volunteer was administered the eye drop formulation of Example 1 for approximately six months. The dosage was two to three drops in the right eye thrice each day for the entire treatment course. The eye drops were administered directly to the center of the eye.

Figure 9A:
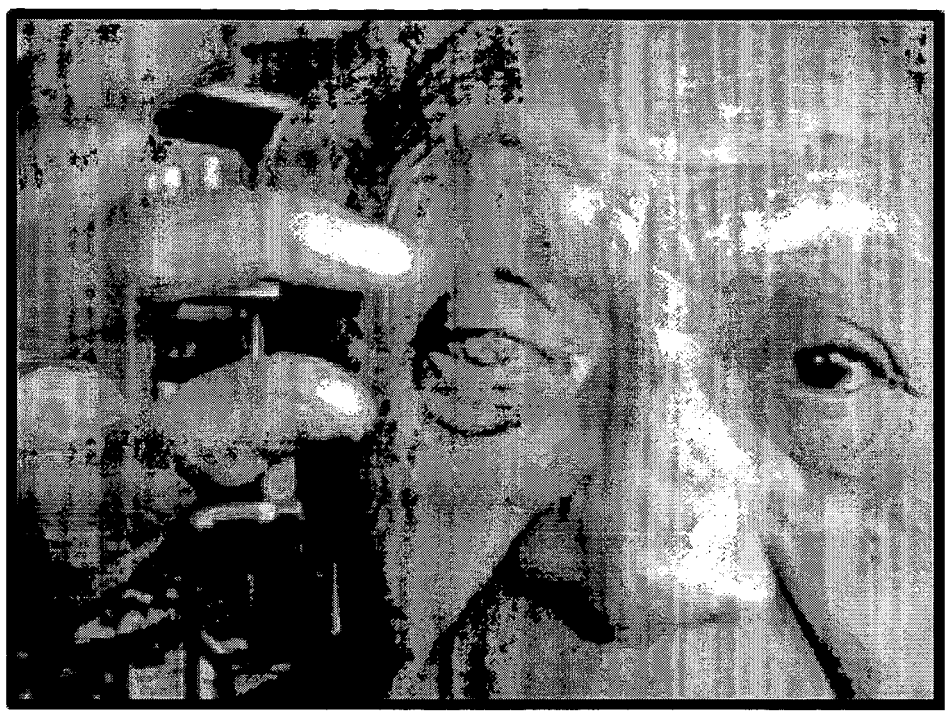
FIG. 9A is a photograph showing a human eye with a traumatic cataract after approximately 2 months of treatment with a pharmaceutical composition comprising Nα-acetyl-L-histidine; (B) close up photo of the eye in (A).
Figure 9B:

Prior to the treatment course, the volunteer's right eye was completely (100%) opaque. Over the course of treatment, his vision started to improve. Two months into the treatment course, the volunteer's cataracts were starting to break up (FIGS. 9A-B). At about the same time, the volunteer was able to see a small red light on his television set from across the room, whereas prior to treatment he was blind in the right eye. As time progressed, the volunteer's vision improved enough such that he could discern coins at three feet distance and could visualize forms from greater distances.

The volunteer's eye sight was not completely restored at the end of the six month treatment course; however, this is likely due to the substantial atrophy of the optic nerve over the 20 year duration of the traumatic cataract.

The next Example describes treatment of human volunteers for a duration sufficient to ameliorate signs and symptoms associated with cataracts.

Example 12

Ophthalmic Administration of a Pharmaceutical Composition Comprising Nα-acetyl-L-histidine for the Treatment of Cataracts in Humans A clinical trial using a formulation as described in Example 6 is underway in the Tijuana metropolitan area. Fifty patients with cataracts were enlisted in a 90 day study. Preliminary reports from the doctors supervising the study show that most of the patients had some improvement after only a few weeks.

The next Example describes treatment of human volunteers for a duration sufficient to eliminate signs associated with cataracts, nuclear sclerosis or dry eye.

Example 13

Ophthalmic Administration of a Pharmaceutical Composition Comprising Nα-acetyl-L-histidine for the Treatment of Cataracts Nuclear Sclerosis or Dry Eye in Humans Healthy human volunteers and those suffering from cataracts, nuclear sclerosis or dry eye are recruited for participation in the following experiment. A first group of volunteers, which have one or more symptoms associated with cataracts, nuclear sclerosis or dry eye in one or both eyes (treatment group), is treated with the eye drop formulation prepared in Example 1. The treatment regimen is continued until the symptoms associated with cataracts, nuclear sclerosis or dry eye are substantially diminished or eliminated or until the volunteers no longer have symptoms of eye discomfort or vision impairment. A second group of volunteers, which does not have any symptoms associated with cataracts, nuclear sclerosis or dry eye in either eye (control group 1), is also treated with the eye drop formulation prepared in Example 1. Additionally, a third group of volunteers, which shows one or more symptoms associated with cataracts, nuclear sclerosis or dry eye in one or both eyes (control group 2), is not treated with the eye drop formulation prepared in Example 1, but rather is administered a saline placebo. Volunteers from the treatment group and control group 2 are carefully selected so that the outward manifestation of eye disease is as similar as possible between the two groups. Volunteers in control group 1, are selected such that they have similar physical characteristics to the volunteers in the treatment group and in control group 2.

The volunteers of the treatment group and control group 1 are administered the eye drop formulation of Example 1 for 36 days. The dosage is two drops twice each day for the 36 day treatment course. The eye drops are administered directly to the affected area of the eye. By the end the treatment period, one or more symptoms associated with cataracts, nuclear sclerosis or dry eye are substantially reduced or eliminated in the volunteers of the treatment group whereas the symptoms associated with cataracts, nuclear sclerosis or dry eye either significantly worsen or do not change for volunteers of control group 2 (volunteers receiving placebo only). The volunteers of control group 1 suffer no adverse reaction from the 36 day treatment regimen.

The next Example describes models of dosing and treatment effect using a pharmaceutical composition comprising Nα-acetyl-L-histidine.

Example 14

Modeling Dosing and Treatment Effect

Figure 10:
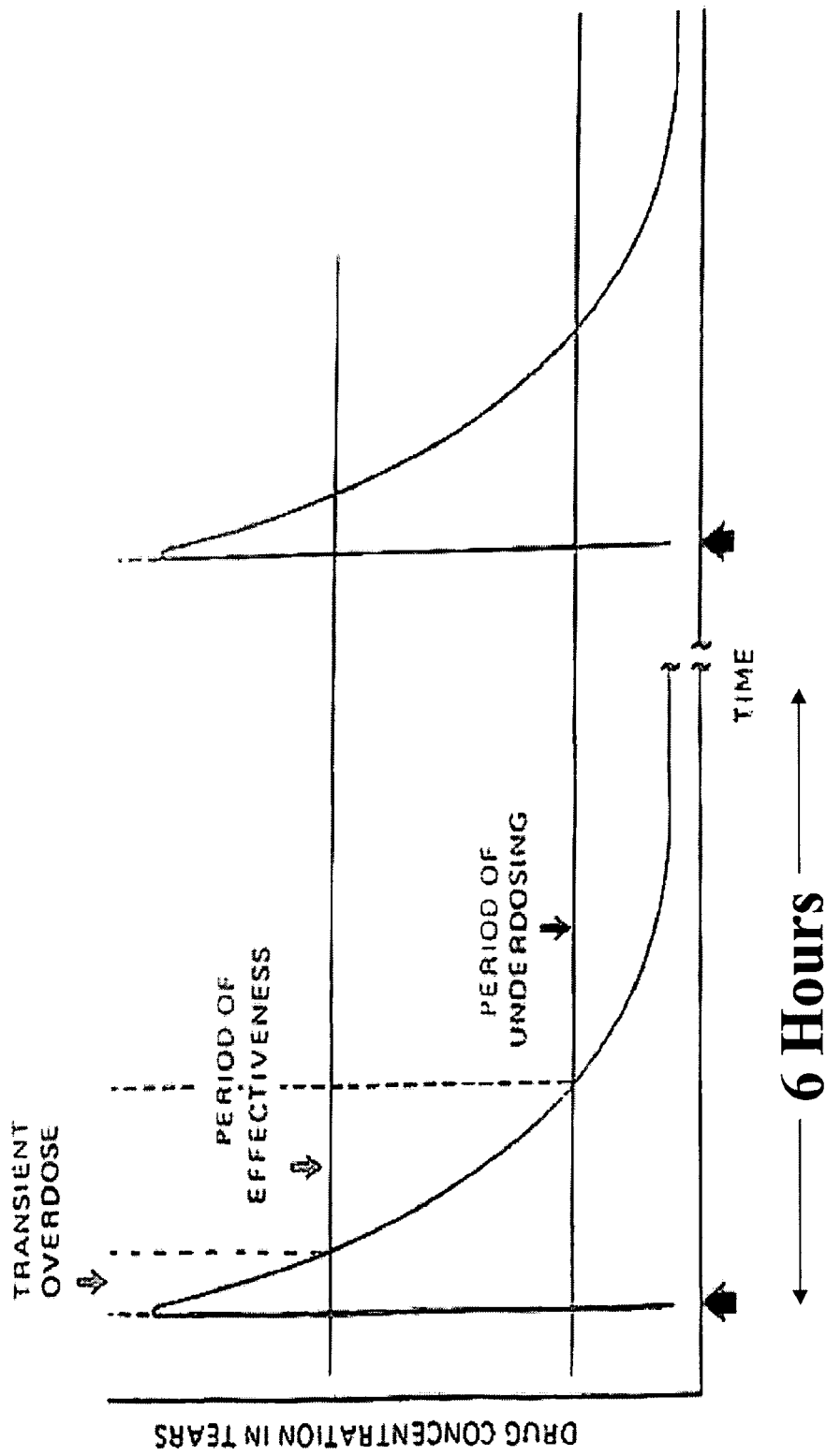
FIG. 10 is graph showing the duration of effective dosing for preparations comprising Nα-acetyl-L-histidine.
Figure 11:
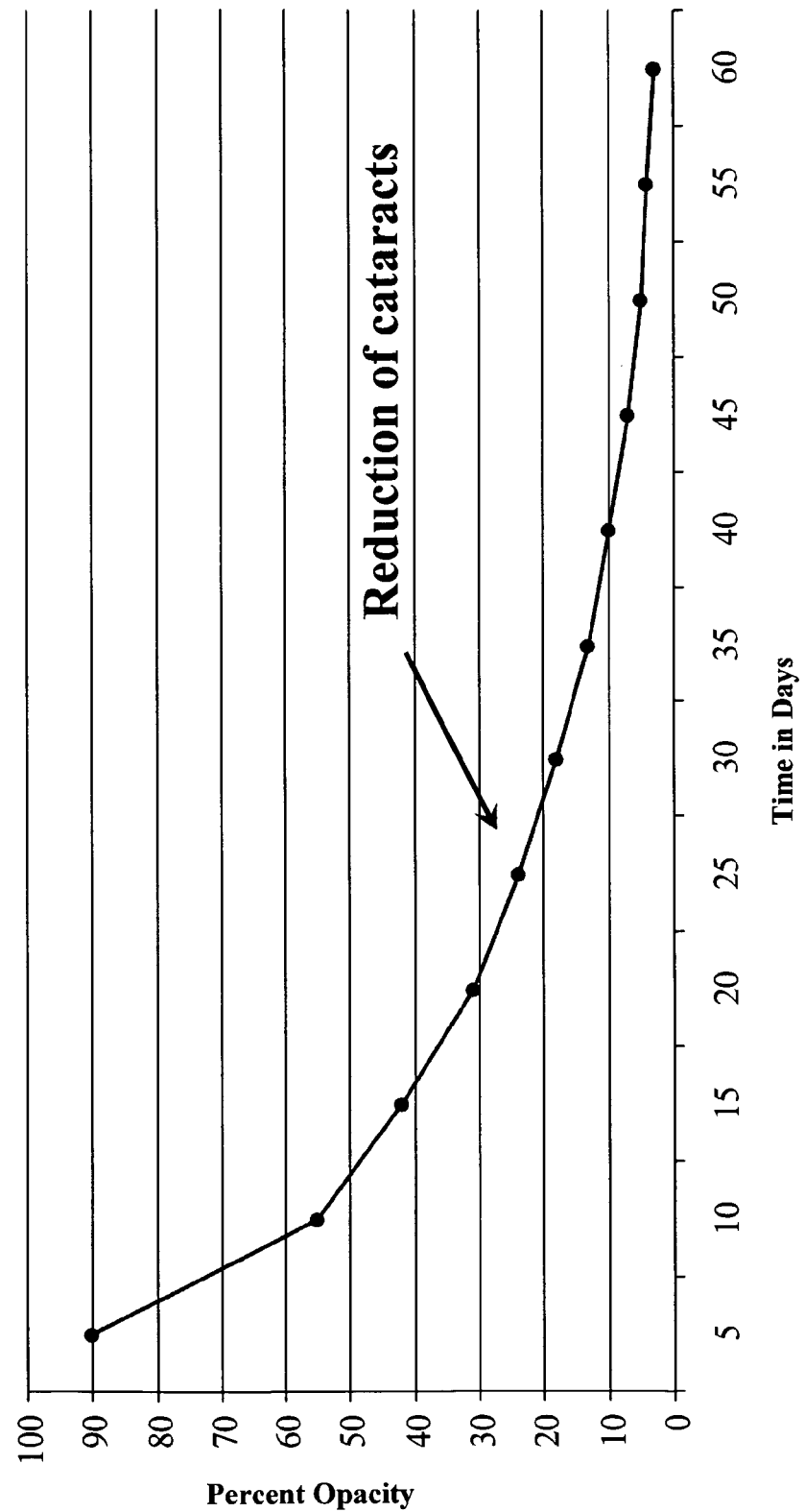
FIG. 11 is a graph which models cataract reduction in response to treatment with preparations comprising Nα-acetyl-L-histidine.

In this Example, the effect of treatment and the duration of effective dosing of preparations containing Nα-acetyl-L-histidine are modeled. FIG. 10 shows a model of the duration of effective dose of an eye drop as described in Example 6. The duration of the dosing is approximately 6 hours and the period of effectiveness is about 2 hours. FIG. 11 is a model of cataract reduction in response to treatment with an eye drop as described in Example 6. This model indicates that a high rate of reduction in opacity occurs in the first few weeks of treatment and the rate of reduction begins to decrease thereafter.

While the invention has been described in some detail for purposes of clarity and understanding, one skilled in the art will appreciate that various changes in form and detail can be made without departing from the true scope of the invention.

All figures, tables, and appendices, as well as patents, applications, and publications, referred to above, are hereby incorporated by reference in their entireties.

What is claimed is:

1. A method of treating an eye disease, said method comprising ophthalmically administering to a subject in need of treatment of said eye disease a therapeutically effective amount of Nα-acetyl-L-histidine and β-alanyl-L-histidine (L-carnosine), wherein said eye disease is selected from the group consisting of cataracts, nuclear sclerosis and dry eyes.

2. The method of claim 1, wherein said Nα-acetyl-L-histidine and β-alanyl-L-histidine (L-carnosine) are administered simultaneously to said subject.

3. The method of claim 2, wherein both Nα-acetyl-L-histidine and β-alanyl-L-histidine (L-carnosine) are administered by providing to said subject a composition which comprises Nα-acetyl-L-histidine and β-alanyl-L-histidine (L-carnosine) each in a concentration from about 0.1% (w/v) to about 30% (w/v).

4. The method of claim 2, wherein both Nα-acetyl-L-histidine and β-alanyl-L-histidine (L-carnosine) are administered by providing to said subject a composition which comprises Nα-acetyl-L-histidine in a concentration of about 1.2% (w/v) and β-alanyl-L-histidine (L-carnosine) in a concentration of about 1% (w/v).

5. The method of claim 2, wherein both Nα-acetyl-L-histidine and β-alanyl-L-histidine (L-carnosine) are administered by providing to said subject a composition which comprises Nα-acetyl-L-histidine in a concentration of about 7.2% (w/v) and β-alanyl-L-histidine (L-carnosine) in a concentration of about 6% (w/v).

6. The method of claim 1, wherein said eye disease is eye cataracts.

7. The method of claim 1, wherein said eye disease is nuclear sclerosis of the eye lens.

8. The method of claim 1, wherein said eye disease is dry eye syndrome.

9. The method of claim 1, wherein said subject is selected from the group consisting of amphibians, reptiles, avians and mammals.

10. The method of claim 9, wherein said mammal is selected from the group consisting of rodents, cats, dogs, pigs, horses and humans.

11. The method of claim 9, wherein said mammal is a human.

12. The method of claim 1, wherein said Nα-acetyl-L-histidine and said L-carnosine are administered at least one time per day.

13. The method of claim 1, wherein said Nα-acetyl-L-histidine and said L-carnosine are administered more than one time per day.

14. The method of claim 1, wherein said therapeutically effective amount of Nα-acetyl-L-histidine ranges from at least about 0.1 mg to at least about 3000 mg.

15. The method of claim 1, wherein said therapeutically effective amount of Nα-acetyl-L-histidine ranges from at least about 1 mg to at least about 2000 mg.

16. The method of claim 1, wherein said therapeutically effective amount of Nα-acetyl-L-histidine is at least about 1200 mg.

17. The method of claim 1, wherein said therapeutically effective amount of Nα-acetyl-L-histidine is at least about 80 mg.

18. The method of claim 1, wherein said Nα-acetyl-L-histidine and said L-carnosine are formulated together in a solution.

19. The method of claim 18, wherein said solution is ophthalmic solution.

20. The method of claim 1, wherein said Nα-acetyl-L-histidine and said L-carnosine are formulated together in an ointment.

21. The method of claim 1, wherein said Nα-acetyl-L-histidine and said L-carnosine are formulated together in a gel.

22. A method of treating an eye disease, said method comprising ophthalmically administering to a subject in need of treatment of said eye disease a therapeutically effective amount of a composition comprising Nα-acetyl-L-histidine, β-alanyl-L-histidine (L-carnosine) and a lubricating agent, wherein said eye disease is selected from the group consisting of cataracts, nuclear sclerosis and dry eyes.

23. The method of claim 22, wherein said composition comprises Nα-acetyl-L-histidine and β-alanyl-L-histidine (L-carnosine) each in a concentration from about 0.1% (w/v) to about 30% (w/v).

24. The method of claim 22, wherein said composition comprises Nα-acetyl-L-histidine in a concentration of about 1.2% (w/v) and β-alanyl-L-histidine (L-carnosine) in a concentration of about 1% (w/v).

25. The method of claim 22, wherein said composition comprises carboxymethylcellulose in a concentration of about 0.5% (w/v), Nα-acetyl-L-histidine in a concentration of about 1.2% (w/v) and 13-alanyl-L-histidine (L-carnosine) in a concentration of about 1% (w/v).

26. The method of claim 22, wherein said composition comprises carboxymethylcellulose in a concentration of about 1% (w/v), Nα-acetyl-L-histidine in a concentration of about 7.2% (w/v) and β-alanyl-L-histidine (L-carnosine) in a concentration of about 6% (w/v).

27. The method of claim 22, wherein said eye disease is eye cataracts.

28. The method of claim 22, wherein said eye disease is nuclear sclerosis of the eye lens.

29. The method of claim 22, wherein said eye disease is dry eye syndrome.

30. The method of claim 22, wherein said subject is selected from the group consisting of amphibians, reptiles, avians and mammals.

31. The method of claim 30, wherein said mammal is selected from the group consisting of rodents, cats, dogs, pigs, horses and humans.

32. The method of claim 30, wherein said mammal is a human.

33. The method of claim 22, wherein said composition is administered at least one time per day.

34. The method of claim 22, wherein said composition is administered more than one time per day.

35. The method of claim 22, wherein said composition is formulated as a solution.

36. The method of claim 35, wherein said solution is an ophthalmic solution.

37. The method of claim 22, wherein said composition is formulated as an ointment.

38. The method of claim 22, wherein said composition is formulated as a gel.

39. A kit for treating an eye disease, said kit comprising a container comprising Nα-acetyl-L-histidine and β-alanyl-L-histidine (L-carnosine) in a pharmaceutically acceptable carrier and instructions for administering said Nα-acetyl-L-histidine and said L-carnosine to a subject in need of treatment of said eye disease, wherein said eye disease is selected from the group consisting of cataracts, nuclear sclerosis and dry eyes.

40. The kit of claim 39, wherein said Nα-acetyl-L-histidine is present in a concentration from about 0.1% (w/v) to about 30% (w/v).

41. The kit of claim 39, wherein said Nα-acetyl-L-histidine is present in a concentration of about 1.2% (w/v).

42. The kit of claim 39, wherein said eye disease is eye cataracts.

43. The kit of claim 39, wherein said eye disease is nuclear sclerosis of the eye lens.

44. The kit of claim 39, further comprising a lubricating agent.

45. The kit of claim 44, wherein said eye disease is dry eye syndrome.

46. The kit of claim 39, wherein said container is a dropper.

47. The kit of claim 39, wherein said container is a tube for dispensing ointment or gel.

48. The method of claim 22, wherein said composition further comprises a preservative.

49. The method of claim 48, wherein said preservative is benzalkonium chloride.

50. The method of claim 22, wherein said lubricating agent comprises carboxymethylcellulose.

51. The kit of claim 39, wherein said container further comprises a preservative.

52. The method of claim 51, wherein said preservative is benzalkonium chloride.

53. The kit of claim 44, wherein said lubricating agent comprises carboxymethylcellulose.

* * * * *